US006515140B2

(12) United States Patent
Albaugh et al.

(10) Patent No.: US 6,515,140 B2
(45) Date of Patent: Feb. 4, 2003

(54) FUSED PYRROLECARBOXAMIDES; A NEW CLASS OF GABA BRAIN RECEPTOR LIGANDS

(75) Inventors: Pamela Albaugh, Clinton, CT (US); Gang Liu, Agoura, CA (US); Kenneth Shaw, Weston, CT (US); Alan Hutchison, Madison, CT (US)

(73) Assignee: Neurogen Corporation, Branford, CT (US)

( * ) Notice: Subject to any disclaimer, the term of this patent is extended or adjusted under 35 U.S.C. 154(b) by 0 days.

(21) Appl. No.: 09/801,956

(22) Filed: Mar. 8, 2001

(65) Prior Publication Data

US 2001/0029299 A1 Oct. 11, 2001

Related U.S. Application Data

(63) Continuation of application No. 09/387,313, filed on Aug. 31, 1999, now Pat. No. 6,211,365, which is a continuation of application No. 09/148,247, filed on Sep. 4, 1998, now Pat. No. 6,080,873, which is a continuation-in-part of application No. 08/588,711, filed on Jan. 19, 1996, now Pat. No. 5,804,686.

(51) Int. Cl.$^7$ .................. C07D 403/12; C07D 405/12; C07D 413/12

(52) U.S. Cl. .................. 548/455; 548/454; 544/105

(58) Field of Search .................. 548/454, 455; 544/105

(56) References Cited

U.S. PATENT DOCUMENTS

| 3,455,943 A | 7/1969 | Remers |
| 4,435,403 A | 3/1984 | Braestrup et al. |
| 4,596,808 A | 6/1986 | Braestrup et al. |
| 4,623,649 A | 11/1986 | Huth et al. |
| 4,719,210 A | 1/1988 | Seidelmann et al. |
| 5,243,049 A | 9/1993 | Shaw et al. |
| 5,266,698 A | 11/1993 | Shaw et al. |
| 5,484,944 A | 1/1996 | Albaugh et al. |
| 5,608,079 A | 3/1997 | Albaugh et al. |

FOREIGN PATENT DOCUMENTS

| DE | 3246932 | 6/1984 |
| WO | 95/11885 | 5/1995 |

OTHER PUBLICATIONS

Bier et al., *Liebigs Ann. Chem.*, pp. 1749–1764. (1986), "Teach assorted benzodiazepine agonist and antagonists and related anti–depressant and central nervous system active compounds."
Carlock et al., *J. Org. Chem.*, vol. 42, No. 11, pp. 1883–1885. (1977), "3–Diazo–4–oxo–3,4–dihydroquinoline. A Novel Synthon for Indole 3–carboxamides."
Carlock et al., *J. Heterocyclic Chem.*, vol. 14, pp. 519–520. (1977), "A Noteworthy Improvement of the 3–Diazo–4–oxo–3,4–dihydroquinoline Photosynthesis of Indole–3–carboxamides."

Primary Examiner—Laura L. Stockton
(74) Attorney, Agent, or Firm—McDonnell Boehnen Hulbert & Berghoff

(57) ABSTRACT

Disclosed are compounds of the formula:

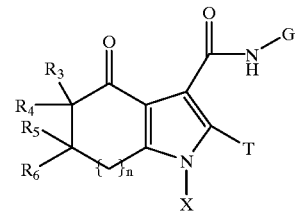

or the pharmaceutically acceptable non-toxic salts thereof wherein:

G, X, T, n, and $R_3$–$R_6$ are as defined herein, which compounds are highly selective agonists, antagonists or inverse agonists for GABAa brain receptors or prodrugs of agonists, antagonists or inverse agonists for GABAa brain receptors. These compounds are useful in the diagnosis and treatment of anxiety, sleep and seizure disorders, overdose with benzodiazepine drugs and for enhancement of memory.

2 Claims, No Drawings

FUSED PYRROLECARBOXAMIDES; A NEW CLASS OF GABA BRAIN RECEPTOR LIGANDS

This is a continuation of application Ser. No. 09/387,313, filed Aug. 31, 1999 now Pat No. 6,211,365, which is a continuation of application Ser. No. 09/148,247, filed Sep. 4, 1998 now Pat. No. 6,080,873, which is a continuation-in-part of application Ser. No. 08/588,711, filed Jan. 19, 1996, U.S. Pat. No. 5,804,686.

BACKGROUND OF THE INVENTION

1. Field of the Invention

This invention relates to novel fused pyrrolecarboxamides which selectively bind to GABAa receptors. This invention also relates to pharmaceutical compositions comprising such compounds. It further relates to the use of such compounds in treating anxiety, sleep and seizure disorders, and overdoses of benzodiazepine-type drugs, and enhancing alertness.

2. Description of the Related Art

γ-Aminobutyric acid (GABA) is regarded as one of the major inhibitory amino acid transmitters in the mammalian brain. Over 30 years have elapsed since its presence in the brain was demonstrated (Roberts & Frankel, J. Biol. Chem 187: 55–63, 1950; Udenfriend, J. Biol. Chem. 187: 65–69, 1950). Since that time, an enormous amount of effort has been devoted to implicating GABA in the etiology of seizure disorders, sleep, anxiety and cognition (Tallman and Gallager, Ann. Rev. Neuroscience 8: 21–44, 1985). Widely, although unequally, distributed through the mammalian brain, GABA is said to be a transmitter at approximately 30% of the synapses in the brain. In most regions of the brain, GABA is associated with local inhibitory neurons and only in two regions is GABA associated with longer projections. GABA mediates many of its actions through a complex of proteins localized both on cell bodies and nerve endings; these are called GABAa receptors. Postsynaptic responses to GABA are mediated through alterations in chloride conductance that generally, although not invariably, lead to hyperpolarization of the cell. Recent investigations have indicated that the complex of proteins associated with postsynaptic GABA responses is a major site of action for a number of structurally unrelated compounds capable of modifying postsynaptic responses to GABA. Depending on the mode of interaction, these compounds are capable of producing a spectrum of activities (either sedative, anxiolytic, and anticonvulsant, or wakefulness, seizures, and anxiety).

1,4-Benzodiazepines continue to be among the most widely used drugs in the world. Principal among the benzodiazepines marketed are chlordiazepoxide, diazepam, flurazepam, and triazolam. These compounds are widely used as anxiolytics, sedative-hypnotics, muscle relaxants, and anticonvulsants. A number of these compounds are extremely potent drugs; such potency indicates a site of action with a high affinity and specificity for individual receptors. Early electrophysiological studies indicated that a major action of benzodiazepines was enhancement of GABAergic inhibition. The benzodiazepines were capable of enhancing presynaptic inhibition of a monosynaptic ventral root reflex, a GABA-mediated event (Schmidt et al., 1967, Arch. Exp. Path. Pharmakol. 258: 69–82). All subsequent electrophysiological studies (reviewed in Tallman et al. 1980, Science 207: 274–81, Haefley et al., 1981, Handb. Exptl. Pharmacol. 33: 95–102) have generally confirmed this finding, and by the mid-1970s, there was a general consensus among electrophysiologists that the benzodiazepines could enhance the actions of GABA.

With the discovery of the "receptor" for the benzodiazepines and the subsequent definition of the nature of the interaction between GABA and the benzodiazepines, it appears that the behaviorally, important interactions of the benzodiazepines with different neurotransmitter systems are due in a large part to the enhanced ability of GABA itself to modify these systems. Each modified system, in turn, may be associated with the expression of a behavior.

Studies on the mechanistic nature of these interactions depended on the demonstration of a high-affinity benzodiazepine binding site (receptor). Such a receptor is present in the CNS of all vertebrates phylogenetically newer than the boney fishes (Squires & Braestrup 1977, Nature 166: 732–34, Mohler & Okada, 1977, Science 198: 854–51, Mohler & Okada, 1977, Br. J. Psychiatry 133: 261–68). By using tritiated diazepam, and a variety of other compounds, it has been demonstrated that these benzodiazepine binding sites fulfill many of the criteria of pharmacological receptors; binding to these sites in vitro is rapid, reversible, stereospecific, and saturable. More importantly, highly significant correlations have been shown between the ability of benzodiazepines to displace diazepam from its binding site and activity in a number of animal behavioral tests predictive of benzodiazepine potency (Braestrup & Squires 1978, Br. J. Psychiatry 133:249–60, Mohler & Okada, 1977, Science 198:854–51, Mohler & Okada, 1977, Br. J. Psychiatry 133:261–68). The average therapeutic doses of these drugs in man also correlate with receptor potency (Tallman et al. 1980, Science 207:274–281).

In 1978, it became clear that GABA and related analogs could interact at the low affinity (1 mM) GABA binding site to enhance the binding of benzodiazepines to the clonazepam-sensitive site (Tallman et al. 1978, Nature, 274:383–85). This enhancement was caused by an increase in the affinity of the benzodiazepine binding site due to occupancy of the GABA site. The data were interpreted to mean that both GABA and benzodiazepine sites were allosterically linked in the membrane as part of a complex of proteins. For a number of GABA analogs, the ability to enhance diazepam binding by 50% of maximum and the ability to inhibit the binding of GABA to brain membranes by 50% could be directly correlated. Enhancement of benzodiazepine binding by GABA agonists is blocked by the GABA receptor antagonist (+) bicuculline; the stereoisomer (−) bicuculline is much less active (Tallman et al., 1978, Nature, 274:383–85).

Soon after the discovery of high affinity binding sites for the benzodiazepines, it was discovered that a triazolopyridazine could interact with benzodiazepine receptors in a number of regions of the brain in a manner consistent with receptor heterogeneity or negative cooperativity. In these studies, Hill coefficients significantly less than one were observed in a number of brain regions, including cortex, hippocampus, and striatum. In cerebellum, triazolopyridazine interacted with benzodiazepine sites with a Hill coefficient of 1 (Squires et al., 1979, Pharma. Biochem. Behav. 10:825–30, Klepner et al. 1979, Pharmacol. Biochem. Behav. 11:457–62). Thus, multiple benzodiazepine receptors were predicted in the cortex, hippocampus, striatum, but not in the cerebellum.

Based on these studies, extensive receptor autoradiographic localization studies were carried out at a light microscopic level. Although receptor heterogeneity has been demonstrated (Young & Kuhar 1980, J. Pharmacol. Exp. Ther. 212:337–46, Young et al., 1981 J. Pharmacol Exp. ther 216:425–430, Niehoff et al. 1982, J. Pharmacol. Exp. Ther. 221:670–75), no simple correlation between localization of receptor subtypes and the behaviors associated with the region has emerged from the early studies. In addition, in the cerebellum, where one receptor was predicted from binding studies, autoradiography revealed heterogeneity of receptors (Niehoffet al., 1982, J. Pharmacol. Exp. Ther. 221:670–75).

A physical basis for the differences in drug specificity for the two apparent subtypes of benzodiazepine sites has been demonstrated by Sieghart & Karobath, 1980, Nature 286:285–87. Using gel electrophoresis in the presence of sodium dodecyl sulfate, the presence of several molecular weight receptors for the benzodiazepines has been reported. The receptors were identified by the covalent incorporation of radioactive flunitrazepam, a benzodiazepine which can covalently label all receptor types. The major labeled bands have molecular weights of 50,000 to 53,000, 55,000, and 57,000 and the triazolopyridazines inhibit labeling of the slightly higher molecular weight forms (53,000, 55,000, 57,000) (Seighart et al. 1983, Eur. J. Pharmacol. 88:291–99).

At that time, the possibility was raised that the multiple forms of the receptor represent "isoreceptors" or multiple allelic forms of the receptor (Tallman & Gallager 1985, Ann. Rev. Neurosci. 8, 21–44). Although common for enzymes, genetically distinct forms of receptors have not generally been described. As we begin to study receptors using specific radioactive probes and electrophoretic techniques, it is almost certain that isoreceptors will emerge as important in investigations of the etiology of psychiatric disorders in people.

The GABAa receptor subunits have been cloned from bovine and human cDNA libraries Schoenfield et al., 1988; Duman et al., 1989). A number of distinct cDNAs were identified as subunits of the GABAa receptor complex by cloning and expression. These are categorized into $\alpha$, $\beta$, $\gamma$, $\delta$, and provide a molecular basis for the GABAa receptor heterogeneity and distinctive regional pharmacology (Shiwers et al., 1980; Levitan et al., 1989). The $\gamma$ subunit appears to enable drugs like benzodiazepines to modify the GABA responses (Pritchett et al., 1989). The presence of low Hill coefficients in the binding of ligands to the GABAa receptor indicates unique profiles of subtype specific pharmacological action.

Drugs that interact at the GABAa receptor can possess a spectrum of pharmacological activities depending on their abilities to modify the actions of GABA. For example, the beta-carbolines were first isolated based upon their ability to inhibit competitively the binding of diazepam to its binding site (Nielsen et al., 1979, Life Sci. 25:679–86). The receptor binding assay is not totally predictive about the biological activity of such compounds; agonists, partial agonists, inverse agonists, and antagonists can inhibit binding. When the beta-carboline structure was determined, it was possible to synthesize a number of analogs and test these compounds behaviorally. It was immediately realized that the beta-carbolines could antagonize the actions of diazepam behaviorally (Tenen & Hirsch, 1980, Nature 288:609–10). In addition to this antagonism, beta-carbolines possess intrinsic activity of their own opposite to that of the benzodiazepines; they become known as inverse agonists.

In addition, a number of other specific antagonists of the benzodiazepine receptor were developed based on their ability to inhibit the binding of benzodiazepines. The best studied of these compounds is an imidazodiazepine (Hunkeler et al., 1981, Nature 290:514–516). This compound is a high affinity competitive inhibitor of benzodiazepine and beta-carboline binding and is capable of blocking the pharmacological actions of both these classes of compounds. By itself, it possesses little intrinsic pharmacological activity in animals and humans (Hunkeler et al., 1981, Nature 290:514–16; Darragh et al., 1983, Eur. J. Clin. Pharmacol. 14:569–70). When a radiolabeled form of this compound was studied (Mohler & Richards, 1981, Nature 294:763–65), it was demonstrated that this compound would interact with the same number of sites as the benzodiazepines and beta-carbolines, and that the interactions of these compounds were purely competitive. This compound is the ligand of choice for binding to GABAa receptors because it does not possess receptor subtype specificity and measures each state of the receptor.

The study of the interactions of a wide variety of compounds similar to the above has led to the categorizing of these compounds. Presently, those compounds possessing activity similar to the benzodiazepines are called agonists. Compounds possessing activity opposite to benzodiazepines are called inverse agonists, and the compounds blocking both types of activity have been termed antagonists. This categorization has been developed to emphasize the fact that a wide variety of compounds can produce a spectrum of pharmacological effects, to indicate that compounds can interact at the same receptor to produce opposite effects, and to indicate that beta-carbolines and antagonists with intrinsic anxiogenic effects are not synonymous.

A biochemical test for the pharmacological and behavioral properties of compounds that interact with the benzodiazepine receptor continues to emphasize the interaction with the GABAergic system. In contrast to the benzodiazepines, which show an increase in their affinity due to GABA (Tallman et al., 1978, Nature 274:383–85, Tallman et al., 1980, Science 207:274–81), compounds with antagonist properties show little GABA shift (i.e., change in receptor affinity due to GABA) (Mohler & Richards 1981, Nature 294:763–65), and the inverse agonists actually show a decrease in affinity due to GABA (Braestrup & Nielson 1981, Nature 294:472–474). Thus, the GABA shift predicts generally the expected behavioral properties of the compounds.

Various compounds have been prepared as benzodiazepine agonists and antagonists. For Example, U.S. Pat. Nos. 3,455,943, 4,435,403, 4,596,808, 4,623,649, and 4,719,210, German Patent No. DE 3,246,932, and Liebigs Ann. Chem. 1986, 1749 teach assorted benzodiazepine agonists and antagonists and related anti-depressant and central nervous system active compounds.

U.S. Pat. No. 3,455,943 discloses compounds of the formula:

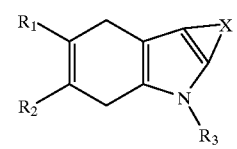

wherein $R_1$ is a member of the group consisting of hydrogen and lower alkoxy; R2 is a member of the group consisting of hydrogen and lower alkoxy; $R_3$ is a member of the group consisting of hydrogen and lower alkyl; and X is a divalent radical selected from the group consisting of

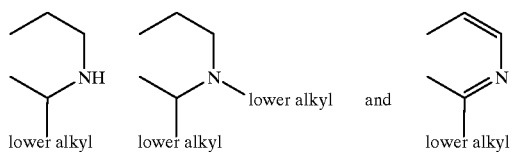

and the non-toxic acid addition salts thereof.

Other references, such as U.S. Pat. No. 4,435,403 and German patent DE 3,246,932 disclose compounds containing the following structural skeleton:

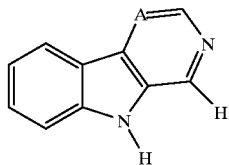

where A is carbon or nitrogen.

A variety of indole-3-carboxamides are described in the literature. For example, J. Org. Chem., 42:1883–1885 (1977) discloses the following compounds.

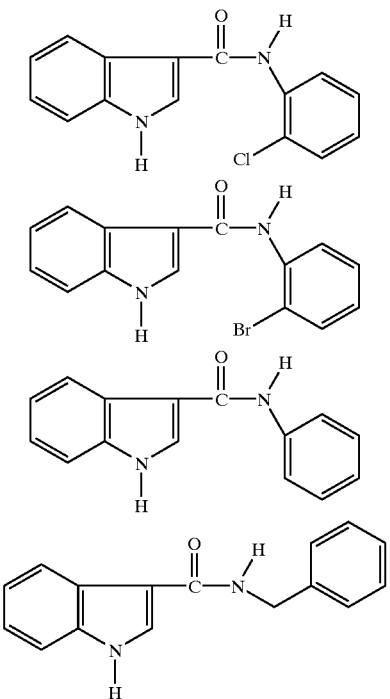

J. Heterocylic Chem. 14:519–520 (1977) discloses a compound of the following formula:

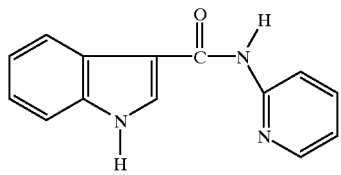

None of these indole-3-carboxamides includes an oxy substituent at the 4-position of the indole ring.

SUMMARY OF THE INVENTION

This invention provides novel compounds of Formula I which interact with a GABAa binding site, the benzodiazepine receptor.

The invention provides pharmaceutical compositions comprising compounds of Formula I. The invention also provides compounds useful in the diagnosis and treatment of anxiety, sleep and seizure disorders, overdose with benzodiazepine drugs and for enhancement of memory. Accordingly, a broad embodiment of the invention is directed to compounds of general Formula I:

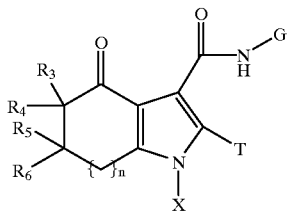

I or the pharmaceutically acceptable non-toxic salts thereof wherein:

G represents

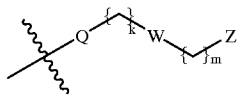

where

Q is phenyl, 2- or 3-thienyl, or 2-, 3-, or 4-pyridyl, all of which may be mono or disubstituted with hydroxy or halogen;

T is halogen, hydrogen, hydroxyl, amino or alkoxy having 1–6 carbon atoms;

W is oxygen, nitrogen, sulfur, or $CR_7R_8$ where $R_7$ and $R_8$ are the same or different and represent hydrogen, alkyl, or $R_7$–$R_8$ taken together represents a cyclic moiety having 3–7 carbon atoms;

X is hydrogen, hydroxyl, or alkyl;

Z is hydroxy, $C_3$–$C_7$ cycloalkyl$C_1$–$C_6$ alkoxy, or $C_1$–$C_6$ alkoxy where the alkyl portion is optionally substituted with amino, mono- or di$C_1$–$C_6$alkylamino, or aza$C_1$–$C_6$cycloalkyl;

amino, or mono- or di$C_1$–$C_6$alkylamino, (trifluoromethyl) methyl, $C_3$–$C_7$ cycloalkyl optionally substituted with $C_1$–$C_6$ alkyl, or $C_3$–$C_7$cycloalkyl$C_1$–$C_6$alkyl;

phenyl or phenyl($C_1$–$C_6$)alkyl where the phenyl portion is optionally substituted with $C_1$–$C_6$ alkyl, hydroxy, $C_1$–$C_6$ alkoxy, triflouromethyl, halogen, amino, or mono- or di$C_1$–$C_6$ alkylamino;

2-, 3-, or 4-pyridyl, 1- or 2-imidazolyl, 1-, 2-, or 3-pyrrolyl, or adamantane-2-yl; each of which may be substituted on a tertiary carbon or a secondary nitrogen with $C_1$–$C_6$alkyl;

$NR_9COR_{10}$ where $R_9$ and $R_{10}$ are the same or different and represent hydrogen or $C_1$–$C_6$ alkyl or $C_3$–$C_7$ cycloalkyl; or Z is connected, optionally through W, to Q to from a 1–6 membered ring; or Z represents
a group of the formula:

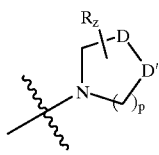

where
p is 1, 2, or 3;
D and D' independently represent oxygen, $NR_y$ or $CHR_y$ provided that only one of D and D' may be $NR_y$ where each $R_y$ is hydrogen or $C_1$–$C_6$ alkyl; or and
$R_z$ is hydrogen or $C_1$–$C_6$ alkyl;
a group of the formula;

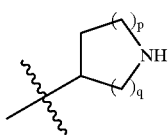

where
p is 1, 2, or 3;
q is 0, 1, or 2;
$R_z$ is hydrogen or $C_1$–$C_6$ alkyl; or
a group of the formula:

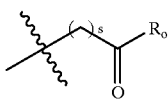

where
s is 0, 1, 2 or 3, and the sum of s and m is not less than 1;
$R_0$ is hydroxy, $C_1$–$C_6$alkoxy, amino, mono- or di$C_1$–$C_6$alkylamino where each alkyl is independently optionally substituted with amino, mono- or di$C_1$–$C_6$alkylamino, or
$R_0$ is a group of the formula

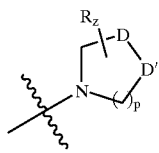

where p, D, D', and $R_z$ are as defined above;

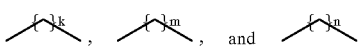

independently represent a carbon chain optionally substituted with hydrogen, halogen, or straight or branched chain lower alkyl having 1–6 carbon atoms;
wherein
k is 0, 1, 2, or 3;
m is 0, 1, 2, or 3; and
n is 0, 1, 2, or 3;

$R_3$, $R_4$, $R_5$, and $R_6$ are the same or different and are selected from hydrogen, alkyl, —$COR_{11}$ or —$CO_2R_{11}$ where $R_{11}$ is alkyl or cycloalkyl having 3–7 carbon atoms; or —$CONR_{12}R_{13}$ where $R_{12}$ and $R_{13}$ are selected independently from hydrogen, alkyl, cycloalkyl having 3–7 carbon atoms, phenyl, 2-, 3-, or 4-pyridyl, or $NR_{12}R_{13}$ forms a heterocyclic group which is morpholinyl, piperidinyl, pyrrolidinyl, or N-alkyl piperazinyl; or $R_3$–$R_4$ may be taken together to form a cyclic moiety having 3–7 carbon atoms; or $R_5$–$R_6$ may be taken together to form a cyclic moiety having 3–7 carbon atoms; and where each alkyl group forming an $R_3$, $R_4$, $R_5$, or $R_6$ substitutent or portion thereof may be substituted independently with hydroxy or mono- or dialkylamino where each alkyl is independently alkyl or cycloalkyl having 3–7 carbon atoms.

These compounds are highly selective agonists, antagonists or inverse agonists for GABAa brain receptors or prodrugs of agonists, antagonists or inverse agonists for GABAa brain receptors. In other words, while the compounds of the invention all interact with GABAa brain receptors, they do not display identical physiologic activity. Thus, these compounds are useful in the diagnosis and treatment of anxiety, sleep and seizure disorders, overdose with benzodiazepine drugs and for enhancement of memory. For example, these compounds can be used to treat overdoses of benzodiazepine-type drugs as they would competitively bind to the benzodiazepine receptor.

DETAILED DESCRIPTION OF THE INVENTION

The novel compounds encompassed by the instant invention can be described by general formula I set forth above or the pharmaceutically acceptable non-toxic salts thereof.

In addition, the present invention encompasses compounds of Formula II.

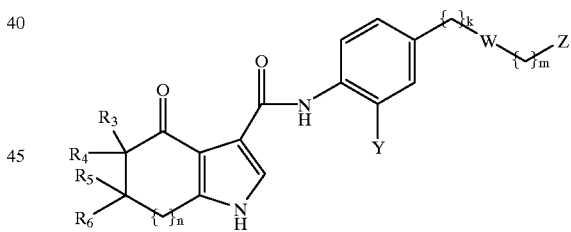

II wherein Y is hydrogen, halogen, or hydroxy; and W, Y, Z, k, m, n, $R_3$, $R_4$, $R_5$, and $R_6$ are defined as above.

The present invention also encompasses compounds of Formula III

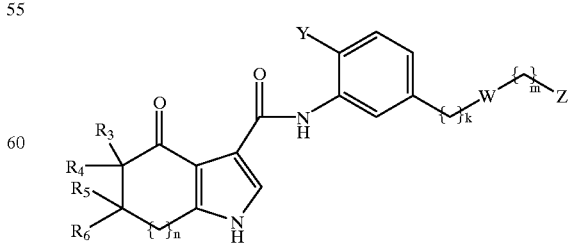

III wherein Y is hydrogen, halogen, or hydroxy; and W, Y, Z, k, m, n, $R_3$, $R_4$, $R_5$, and $R_6$ are defined as above.

The present invention also encompasses compounds of Formula IV, IVa, IVb, and IVc.

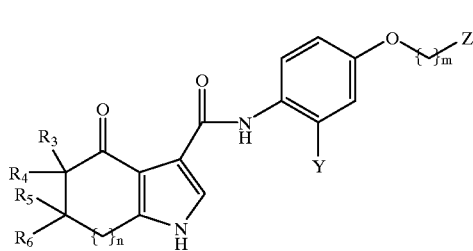

IV

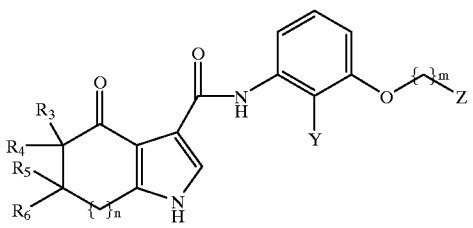

IVa

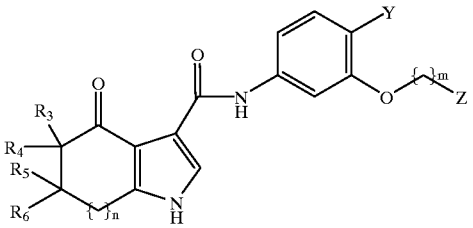

IVb

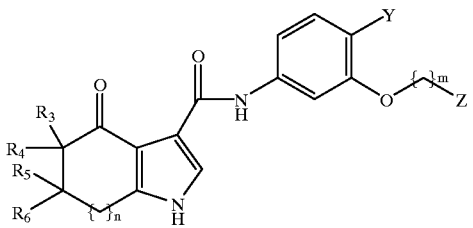

IVc wherein Y is hydrogen, halogen, or hydroxy; and W, Y, Z, k, m, n, $R_3$, $R_4$, $R_5$, and $R_6$ are defined as above.

The present invention also encompasses compounds of Formula V.

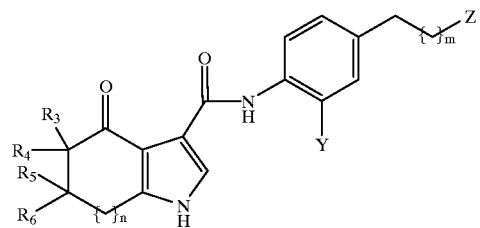

V wherein Y is hydrogen, halogen, or hydroxy; and W, Y, Z, k, m, n, $R_3$, $R_4$, $R_5$, and $R_6$ are defined as above.

The present invention also encompasses compounds of Formula VI.

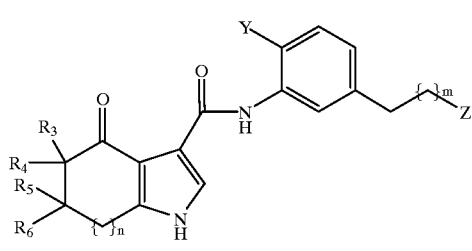

VI wherein Y is hydrogen, halogen, or hydroxy; and W, Y, Z, k, m, n, $R_3$, $R_4$, $R_5$, and $R_6$ are defined as above.

The present invention also encompasses compounds of Formula VII.

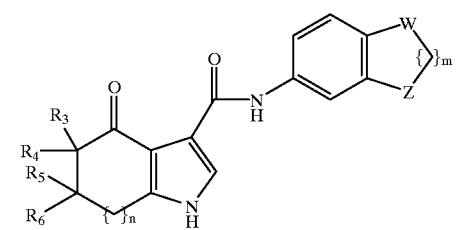

VII wherein W, Z, m, n, $R_3$, $R_4$, $R_5$, and $R_6$ are defined as above.

The present invention also encompasses compounds of Formula VIII.

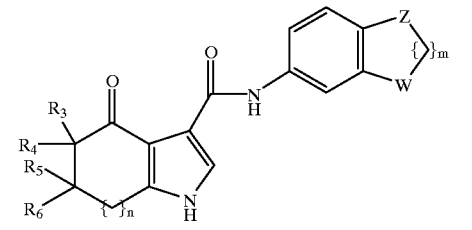

VIII wherein W, Z, m, n, $R_3$, $R_4$, $R_5$, and $R_6$ are defined as above.

The present invention also encompasses compounds of Formula IX.

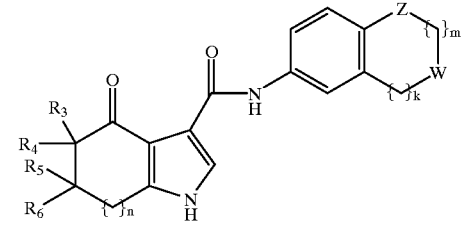

IX wherein W, Z, k, m, n, $R_3$, $R_4$, $R_5$, and $R_6$ are defined as above.

The present invention also encompasses compounds of Formula X.

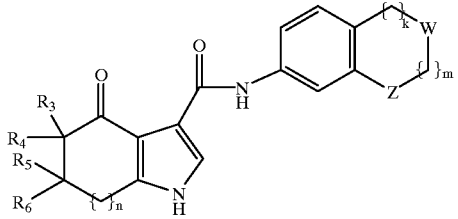

wherein W, Z, k, m, n, $R_3$, $R_4$, $R_5$, and $R_6$ are defined as above.

Preferred compounds of the invention are those where n is 1 or 2. Particularly preferred are those where X and T are both hydrogen. Thus, preferred compounds of the invention have formulas Ia and Ib.

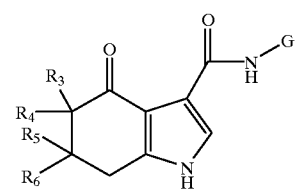

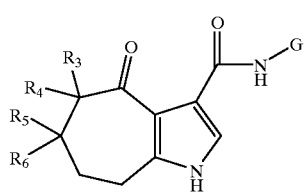

Preferred G substituents of the invention include the following:

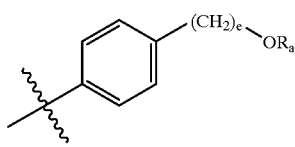

where $R_a$ represents hydrogen or alkyl where the alkyl is optionally halogenated; and e is an integer of 1–3.

More preferred G substituents of formula A include those where e is 1, 2, or 3, and $R_a$ is hydrogen, methyl, ethyl, isopropyl, or cyclopropyl. Particularly preferred G substituents of formula A include those where e is 1, 2, or 3, and $R_a$ is hydrogen or methyl.

Another preferred G substituent is the following formula:

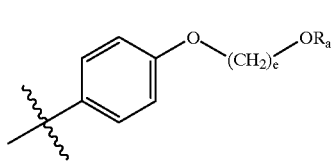

where $R_a$ represents hydrogen or alkyl where the alkyl is optionally halogenated; and e is an integer of 1–3.

More preferred G substituents of formula B include those where e is 1, 2, or 3; and $R_a$ is hydrogen, methyl or ethyl. Particularly preferred G substituents of formula B include those where e is 1 or 2, and $R_a$ is hydrogen or methyl.

Another preferred G substituent is the following formula:

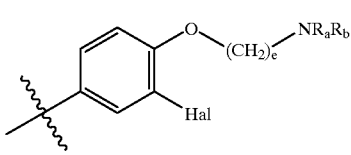

where

Hal represents a halogen, preferably fluoro, bromo, or chloro;

$R_a$ and $R_b$ independently represent hydrogen, $C_1$–$C_6$ alkyl, $C_3$–$C_7$cycloalkyl, $C_3$–$C_7$cycloalkyl$C_1$–$C_6$alkyl where the cycloalkyl group may be substituted with halogen, $C_1$–$C_6$ alkyl, $C_1$–$C_6$ alkoxy, or mono- or di$C_1$–$C_6$ alkylamino; and e is an integer of 2–3.

Preferred compounds having formula C as the G group include those where Hal is fluoro and e is 2, 3, or 4.

More preferred G substituents of formula C include those where $R_a$ is hydrogen, methyl or ethyl; and $R_b$ is hydrogen. Particularly preferred G substituents of formula C include those where e is 2; $R_a$ is hydrogen or methyl; and $R_b$ is hydrogen.

Another preferred G substituent is the following formula:

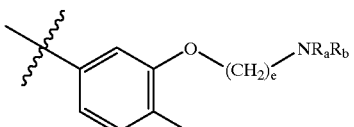

where

Hal represents a halogen, preferably fluoro, bromo, or chloro;

$R_a$ and $R_b$ independently represent hydrogen, $C_1$–$C_6$ alkyl $C_3$–$C_7$cycloalkyl, $C_3$–$C_7$cycloalkyl$C_1$–$C_6$alkyl where the cycloalkyl group may be substituted with halogen, $C_1$–$C_6$ alkyl, $C_1$–$C_6$ alkoxy, or mono- or di$C_1$–$C_6$ alkylamino; and e is an integer of 2–3.

Preferred compounds having formula C-1 as the G group include those where Hal is fluoro and e is 2, 3, or 4.

Another preferred G substituent is the following formula:

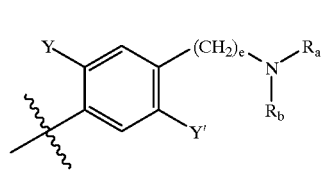

where $R_a$ represents hydrogen, alkyl, or $C_{3-7}$ cycloalkyl, or a group of the formula:

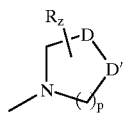

where
p is 1, 2, or 3;
D and D' independently represent oxygen, $NR_y$ or $CHR_y$, provided that only one of D and D' may be $NR_y$, where each $R_y$ is hydrogen or $C_1-C_6$ alkyl; and
$R_z$ is hydrogen or $C_1-C_6$ alkyl; and
$R_b$ represents hydrogen, alkyl, or acyl;
Y and Y' independently represent hydrogen or halogen; and
e is an integer of 1–3.

More preferred G substituents of formula D are those where Y is hydrogen or fluorine; and e is 1 or 2. Particularly preferred G substituents of formula D are those where Y is hydrogen or fluorine; e is 1 or 2; $R_a$ is hydrogen, $C_{1-3}$ alkyl, or cyclopropyl, and $R_b$ is hydrogen, methyl, or acyl. Other particularly preferred G substituents of formula D are those where Y is hydrogen and Y' is fluorine. Still other particularly preferred G groups of Formula D are those where e is 1 or 2; $R_a$ is hydrogen, $C_{1-3}$ alkyl, cyclopropyl or cyclopropylmethyl, and $R_b$ is hydrogen, methyl, or acyl.

Another preferred G substituent is the following formula:

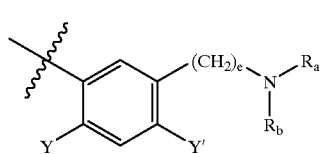

D-1 where $R_a$ represents hydrogen, alkyl, or $C_{3-7}$ cycloalkyl; and
$R_b$ represents hydrogen, alkyl, or acyl; or
$R_a$ and $R_b$ independently represent hydrogen, $C_1-C_6$ alkyl, $C_{3-7}$cycloalkyl$C_1-C_6$alkyl; and
Y and Y' independently represent hydrogen or halogen; and
e is an integer of 1–3.

More preferred G substituents of formula D are those where Y is hydrogen or fluorine; and e is 1 or 2. Particularly preferred G substituents of formula D are those where Y is hydrogen or fluorine; e is 1 or 2; $R_a$ is hydrogen, $C_{1-3}$ alkyl, or cyclopropyl, and $R_b$ is hydrogen, methyl, or acyl. Other particularly preferred G substituents of formula D are those where Y is hydrogen and Y' is fluorine. Still other particularly preferred G groups of Formula D are those where e is 1 or 2; $R_a$ is hydrogen, $C_{1-3}$ alkyl, cyclopropyl or cyclopropylmethyl, and $R_b$ is hydrogen, methyl, or acyl.

Another preferred G substituent is the following formula:

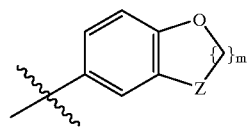

E where Z is oxygen, nitrogen, or methylene; and m is 1 or 2.
Particularly preferred G substituents of formula E are those where Z is oxygen, and m is 1 or 2. Other particularly preferred G substituents of formula E are those where Z is nitrogen, and m is 1 or 2.

Another preferred G substituent is the following formula:

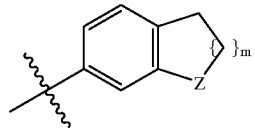

F where Z is oxygen or nitrogen; and m is 1 or 2.
Particularly preferred G substituents of formula F are those where Z is nitrogen, and m is 1 or 2.

Another preferred G substituent is the following formula:

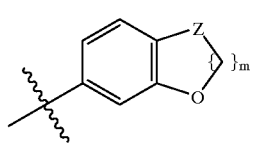

H where Z is oxygen, nitrogen, or methylene; and m is 1 or 2.
Particularly preferred G substituents of formula H are those where Z is nitrogen, and m is 1 or 2.

Another preferred G substituent is the following formula:

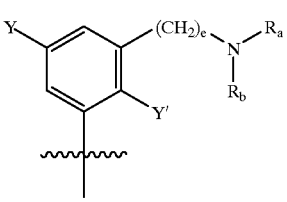

J where $R_a$ represents hydrogen, alkyl, or $C_{3-7}$ cycloalkyl;
$R_b$ represents hydrogen, alkyl, or acyl;
Y and Y' independently represent hydrogen or halogen; and
e is an integer of 1–3.

More preferred G substituents of formula J are those where Y and Y' are independently hydrogen or fluorine; and e is 1 or 2. Particularly preferred G substituents of formula J are those where and Y' are independently hydrogen or fluorine; e is 1 or 2; $R_a$ is hydrogen, $C_{1-3}$ alkyl, or cyclopropyl, and $R_b$ is hydrogen, methyl, or acyl.

Another preferred G substituent is the following formula:

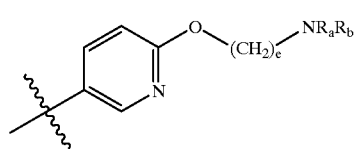

K where
$R_a$ and $R_b$ independently represent hydrogen, $C_{1-6}$ alkyl, $C_3-C_7$cycloalkyl, $C_3-C_7$cycloalkyl$C_1-C_6$alkyl where the cycloalkyl group may be substituted with halogen, $C_1-C_6$ alkyl, $C_1-C_6$ alkoxy, or mono- or di$C_1-C_6$ alkylamino; and
e is an integer of 2–3.

Another preferred G substituent is represented by the following formula:

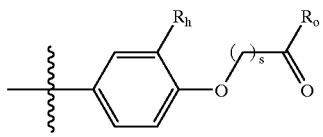
M where
$R_h$ is hydrogen, halogen, $C_1$–$C_6$alkyl, $C_1$–$C_6$alkoxy, or trifluoromethyl;
s is 0, 1, 2 or 3, and the sum of s and m is not less than 1;
$R_0$ is hydroxy, $C_1$–$C_6$alkoxy, amino, mono- or di$C_1$–$C_6$alkylamino where each alkyl is independently optionally substituted with amino, mono- or di$C_1$–$C_6$alkylamino, or
$R_0$ is a group of the formula

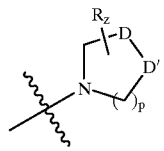

p is 1, 2, or 3;
D and D' independently represent oxygen, $NR_y$ or $CHR_y$, provided that only one of D and D' may be $NR_y$, where each $R_y$ is hydrogen or $C_1$–$C_6$ alkyl; or and
$R_z$ is hydrogen or $C_1$–$C_6$ alkyl.
Preferred M groups are those where $R_h$ is hydrogen or halogen, most preferably fluoro, and $R_0$ is a group of the formula:

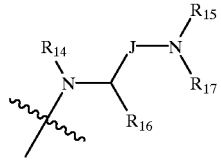

where
$R_{14}$ is hydrogen or $C_1$–$C_6$alkyl;
$R_5$ is hydrogen or $C_1$–$C_6$alkyl;
$R_{16}$ is hydrogen, ethyl, or methyl;
$R_{17}$ is $C_1$–$C_6$alkyl; and
J is a $C_1$–$C_4$ alkylene group, preferably methylene, ethylene, or propylene.

Particularly preferred groups of Formula M include those where s is 1 and $R_0$ is ethoxy, hydroxy, ethylamino, diethylamino, morpholinyl, piperazinyl, 4-methylpiperazinyl,

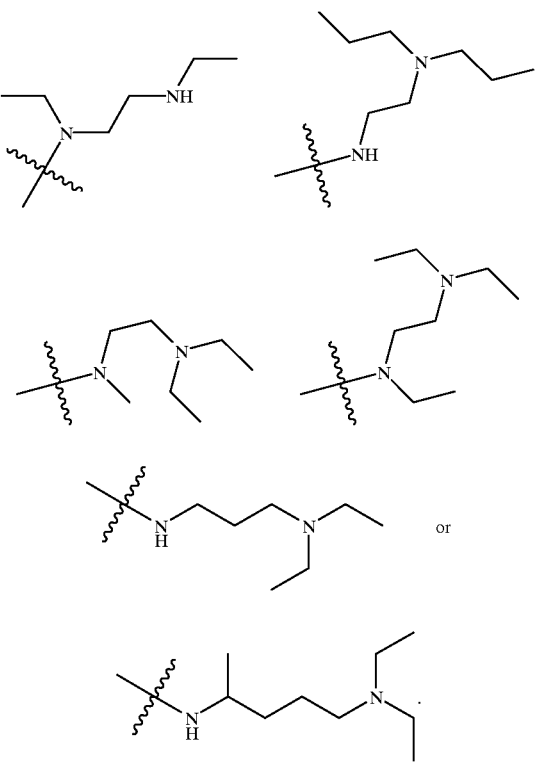

Representative compounds of the invention are shown below in Table 1.

TABLE 1

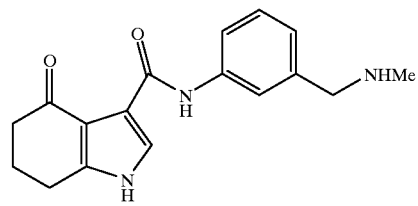

Compound 1

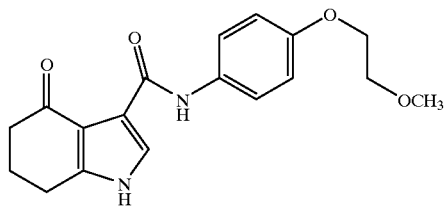

Compound 2

TABLE 1-continued
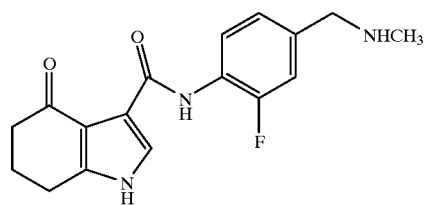
Compound 3
Compound 4
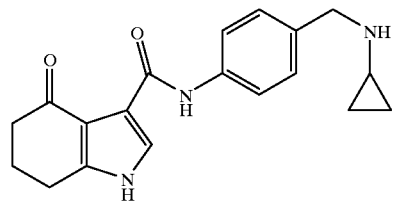
Compound 5
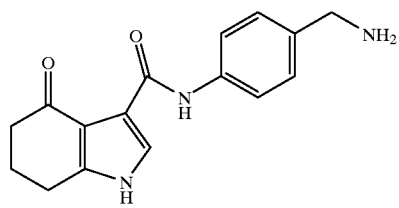
Compound 6
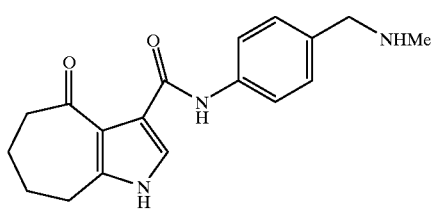
Compound 7
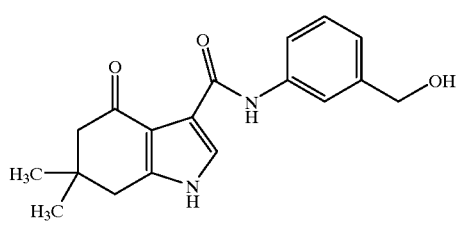
Compound 8

TABLE 1-continued
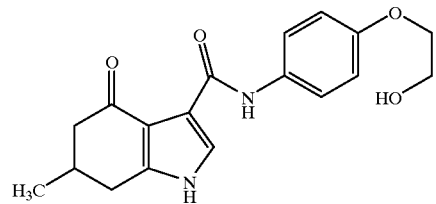
Compound 9
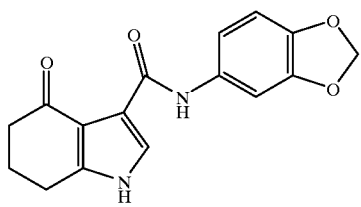
Compound 10
Compound 11
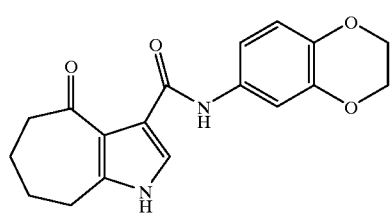
Compound 12
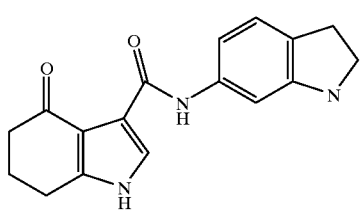
Compound 13
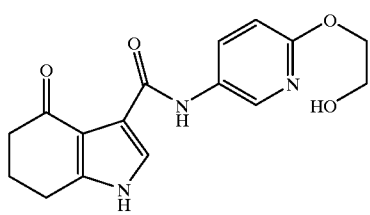
Compound 14

TABLE 1-continued
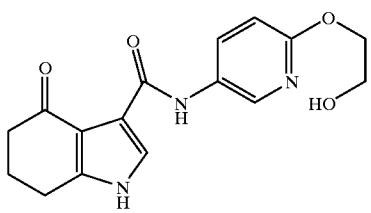
Compound 15
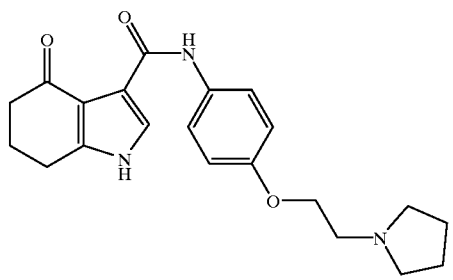
Compound 47
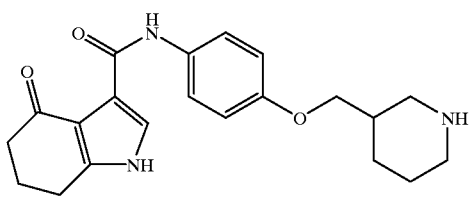
Compound 86
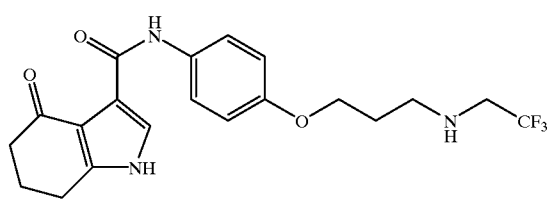
Compound 95
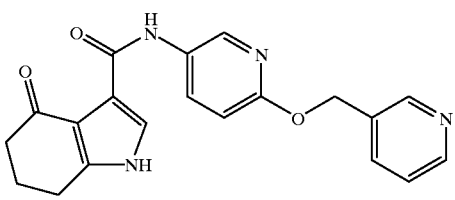
Compound 115
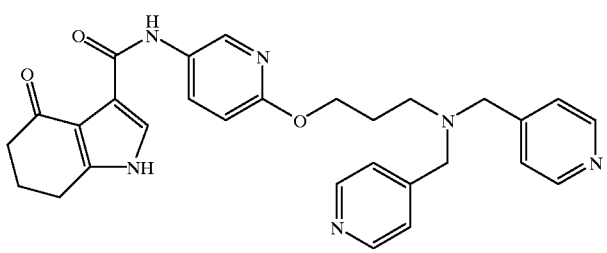
Compound 145

TABLE 1-continued
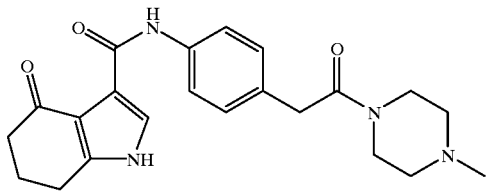
Compound 148
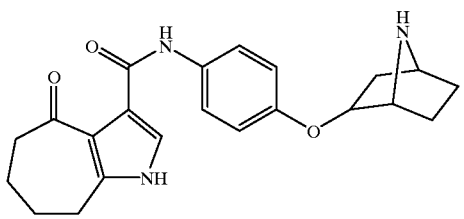
Compound 149
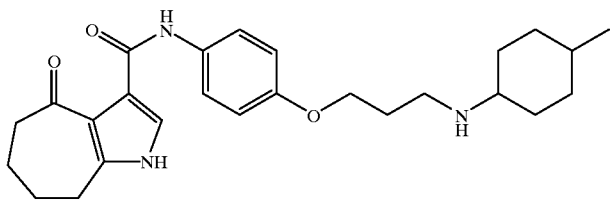
Compound 179
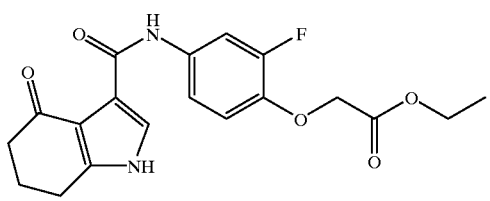
Compound 222
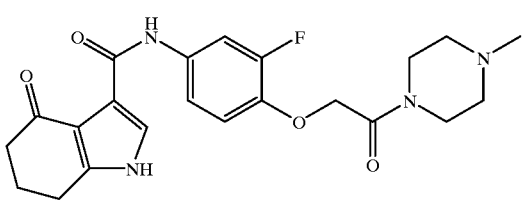
Compound 226

TABLE 1-continued

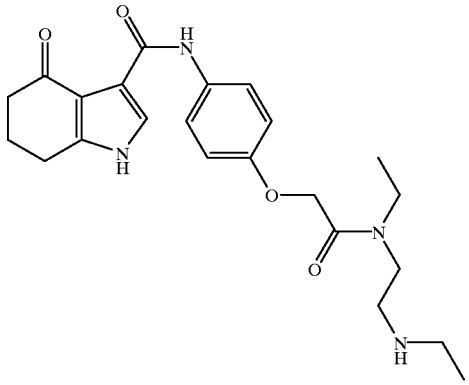

Compound 227

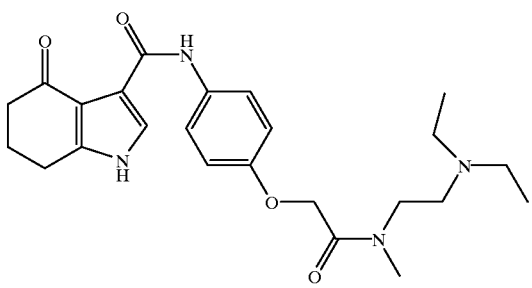

Compound 229

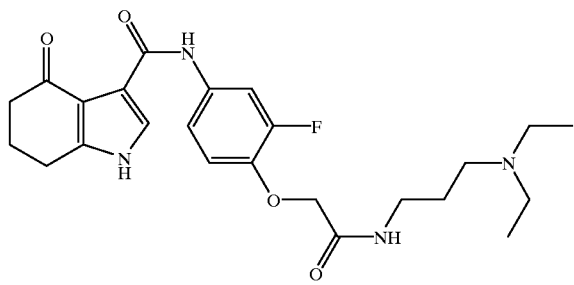

Compound 235

The following numbering conventions are used to identify positions on the ring systems in the compounds of the invention:

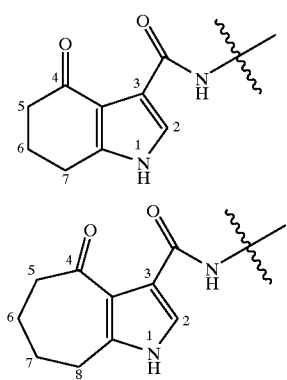

Representative compounds of the present invention, which are encompassed by Formula I, include, but are not limited to the compounds in Table I and their pharmaceutically acceptable salts. Non-toxic pharmaceutically acceptable salts include salts of acids such as hydrochloric, phosphoric, hydrobromic, sulfuric, sulfinic, formic, toluenesulfonic, methanesulfonic, nitric, benzoic, citric, tartaric, maleic, hydroiodic, alkanoic such as acetic, $HOOC-(CH_2)_n-COOH$ where n is 0–4, and the like. Those skilled in the art will recognize a wide variety of non-toxic pharmaceutically acceptable addition salts.

Representative compounds of the present invention, which are encompassed by Formula I, include, but are not limited to the compounds in Table 1 and their pharmaceutically acceptable salts. The present invention also encompasses the acylated prodrugs of the compounds of Formula I. Those skilled in the art will recognize various synthetic methodologies which may be employed to prepare non-toxic pharmaceutically acceptable addition salts and acylated prodrugs of the compounds encompassed by Formula I.

By "alkyl" or "lower alkyl" in the present invention is meant straight or branched chain alkyl groups having 1–6 carbon atoms, such as, for example, methyl, ethyl, propyl, isopropyl, n-butyl, sec-butyl, tert-butyl, pentyl, 2-pentyl, isopentyl, neopentyl, hexyl, 2-hexyl, 3-hexyl, and 3-methylpentyl.

By "alkoxy" or "lower alkoxy" in the present invention is meant straight or branched chain alkoxy groups having 1–6 carbon atoms, such as, for example, methoxy, ethoxy, propoxy, isopropoxy, n-butoxy, sec-butoxy, tert-butoxy, pentoxy, 2-pentyl, isopentoxy, neopentoxy, hexoxy, 2-hexoxy, 3-hexoxy, and 3-methylpentoxy.

By "diC$_1$–C$_6$alkylamnino" is meant an amino group carrying two C$_1$–C$_6$alkyl groups that are the same or different.

By "benzoxazinyl" as used herein is meant a moiety of the formula:

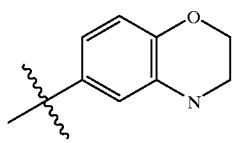

A benzoxazin-6-yl group is depicted.

By "halogen" in the present invention is meant fluorine, bromine, chlorine, and iodine.

By "2-hydroxyethoxy" is meant a group of the formula: —OCH$_2$CH$_2$OH.

By a 2-, 3-, or 4-pyridyl, 1- or 2-imidazolyl, 1-, 2-, or 3-pyrrolyl, or adamantane-2-yl group that is substituted on a tertiary carbon or a secondary nitrogen with C$_1$–C$_6$alkyl is meant any such group in which a hydrogen atom is replaced with an appropriate alkyl group. By way of example, such groups include the following:

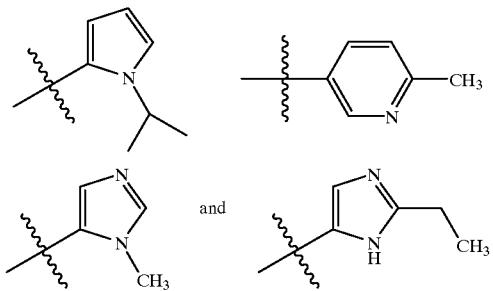

By "N-alkylpiperazyl" in the invention is meant radicals of the formula:

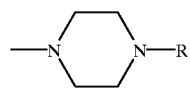

where R is a straight or branched chain lower alkyl as defined above.

The pharmaceutical utility of compounds of this invention are indicated by the following assay for GABAa receptor binding activity.

Assays are carried out as described in Thomas and Tallman (J. Bio. Chem. 156:9838–9842, J. Neurosci. 3:433–440, 1983). Rat cortical tissue is dissected and homogenized in 25 volumes (w/v) of 0.05 M Tris HCl buffer (pH 7.4 at 4° C.). The tissue homogenate is centrifuged in the cold (4°) at 20,000×g for 20'. The supernatant is decanted and the pellet is rehomogenized in the same volume of buffer and again centrifuged at 20,000×g. The supernatant is decanted and the pellet is frozen at −20° C. overnight. The pellet is then thawed and rehomogenized in 25 volume (original wt/vol) of buffer and the procedure is carried out twice. The pellet is finally resuspended in 50 volumes (w/vol of 0.05 M Tris HCl buffer (pH 7.4 at 40° C.).

Incubations contain 100 ml of tissue homogenate, 100 ml of radioligand 0.5 nM ($^3$H-RO15-1788 [$^3$H-Flumazenil] specific activity 80 Ci/mmol), drug or blocker and buffer to a total volume of 500 ml. Incubations are carried for 30 min at 4° C. then are rapidly filtered through GFB filters to separate free and bound ligand. Filters are washed twice with fresh 0.05 M Tris HCl buffer (pH 7.4 at 4° C.) and counted in a liquid scintillation counter. 1.0 mM diazepam is added to some tubes to determine nonspecific binding. Data are collected in triplicate determinations, averaged and % inhibition of total specific binding is calculated. Total Specific Binding=Total−Nonspecific. In some cases, the amounts of unlabeled drugs is varied and total displacement curves of binding are carried out. Data are converted to Ki's; results for compounds of this invention are listed in Table 2.

TABLE 2

| Compound Number | K$_i$(nM) |
|---|---|
| 1 | 90 |
| 2 | 29 |
| 3 | 49 |
| 4 | 0.24 |
| 5 | 9 |
| 6 | 9 |
| 7 | 30 |
| 8 | 27 |
| 9 | 1.3 |
| 10 | 37 |
| 11 | 7 |
| 12 | 5 |
| 13 | 24 |
| 14 | 3 |
| 15 | 12 |

The compounds of general formula I may be administered orally, topically, parenterally, by inhalation or spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition, there is provided a pharmaceutical formulation comprising a compound of general formula I and a pharmaceutically acceptable carrier. One or more compounds of general formula I may be present in association with one or more non-toxic pharmaceutically acceptable carriers and/or diluents and/or adjuvants and if desired other active ingredients. The pharmaceutical compositions containing compounds of general formula I may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation products of the said partial esters with ethylene oxide, for example polyoxyethylene sorbitan monoleate. The emulsions may also contain sweetening and flavoring agents.

Syrups and elixirs may be formulated with sweetening agents, for example glycerol, propylene glycol, sorbitor or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono-or diglycerides. In addition, fatty acids such as oleic acid find use in the preparation of injectables.

The compounds of general formula I may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

Compounds of general formula I may be administered parenterally in a sterile medium. The drug, depending on the vehicle and concentration used, can either be suspended or dissolved in the vehicle. Advantageously, adjuvants such as local anaesthetics, preservatives and buffering agents can be dissolved in the vehicle.

Dosage levels of the order of from about 0.1 mg to about 140 mg per kilogram of body weight per day are useful in the treatment of the above-indicated conditions (about 0.5 mg to about 7 g per patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

An illustration of the preparation of compounds of the present invention is given in Scheme I.

Scheme I

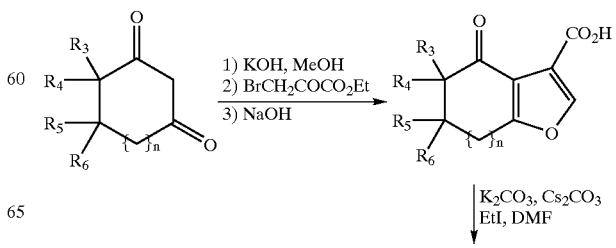

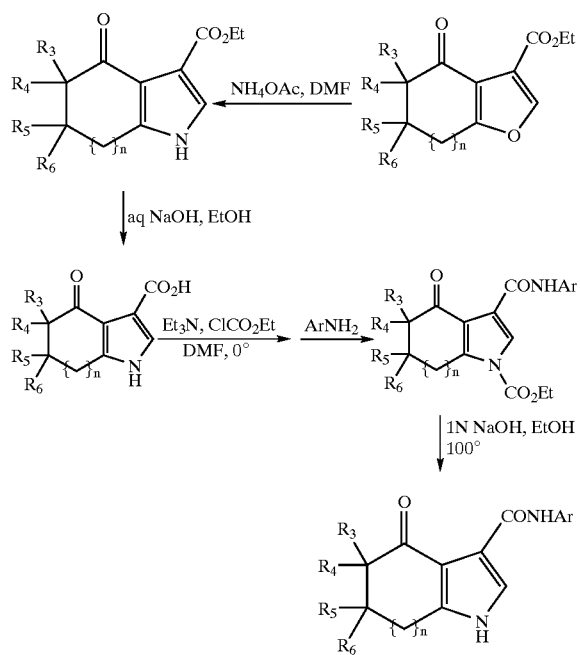

where:

Ar is

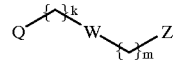

where Q, W, k, m, n, Z, $R_3$, $R_4$, $R_5$, and $R_6$ are as defined above.

Those having skill in the art will recognize that the starting materials may be varied and additional steps employed to produce compounds encompassed by the present invention, as demonstrated by the following examples.

In some cases protection of certain reactive functionalities may be necessary to achieve some of the above transformations. In general the need for such protecting groups will be apparent to those skilled in the art of organic synthesis as well as the conditions necessary to attach and remove such groups. Representative examples of the preparation of various protected aniline derivatives are shown in Schemes II (1), (2) and (3).

Scheme II

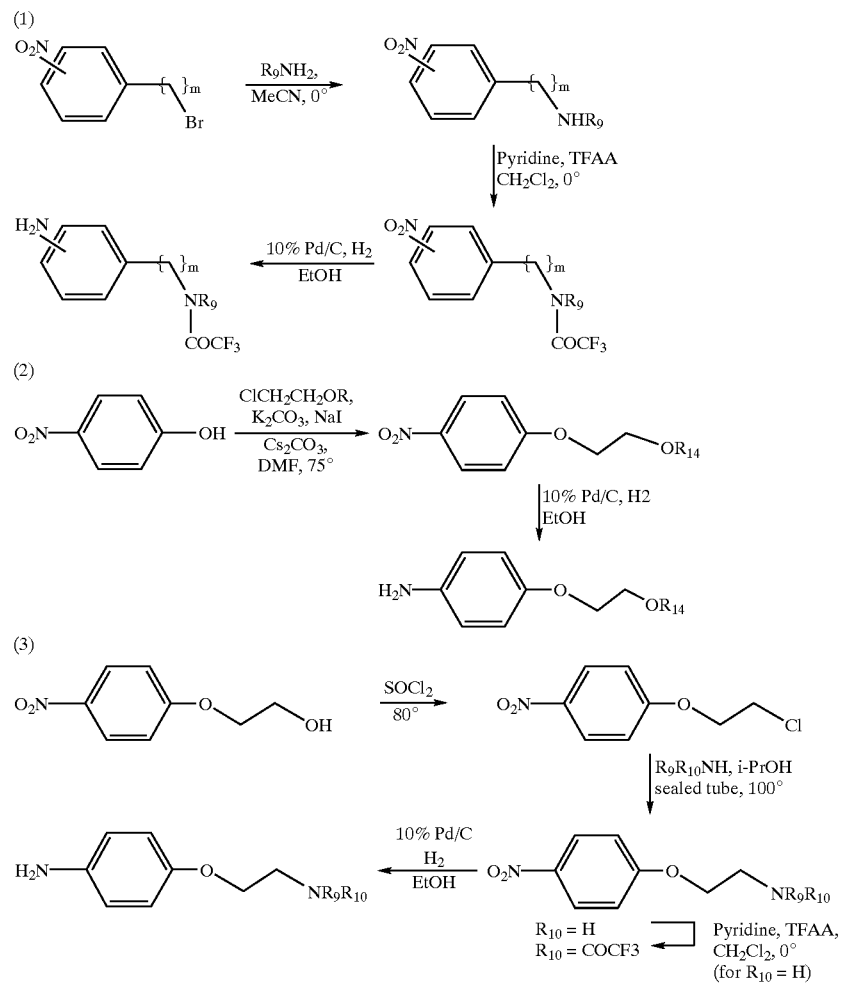

Compounds of Formula I where G is a group of, for example, formulas C, C-1, D, D-1, K or M can be made using the above outlined methods and, e.g., additional ester and amide coupling reactions. In certain situations, protection of the indole ring nitrogen will be necessary.

For example, compounds where $R_0$ is a dialkylamino group can be prepared from a 2-(4-nitrophenoxy)ethan-1-ol made as described above and oxidation of the hydroxy group, and subsequent formation of an acid chloride or active ester. The active ester or acid chloride may then be coupled to an appropriate amine and the resulting nitrophenyl compound used as shown in the above schemes.

The disclosures in this application of all articles and references, including patents, are incorporated herein by reference in their entirety.

One skilled in the art will recognize that modifications may be made in the present invention without deviating from the spirit or scope of the invention. The invention is illustrated further by the following examples which are not to be construed as limiting the invention or scope of the specific procedures or compositions described herein.

EXAMPLE 1

Preparation of starting materials and intermediates

The starting materials and various intermediates may be obtained from commercial sources, prepared from commercially available organic compounds, or prepared using well known synthetic methods.

Representative examples of methods for preparing intermediates of the invention are set forth below.

1. 4-oxo-4,5,6,7-etrahydrobenzofuran-3-carboxylic acid

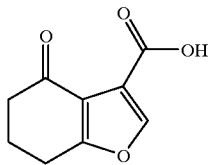

4-Oxo-4,5,6,7-tetrahydrobenzofuran-3-carboxylic acid is prepared according to the following procedure. Potassium hydroxide (345 g, 6.15 mol) is dissolved in methyl alcohol (1.2 L) then cooled in an ice water bath. A solution of cyclohexanedione (714 g, 6.15 mol) in methyl alcohol (1.2 L), dissolved using gentle heat, is added dropwise to the cold, stirred KOH solution over 2 h. A solution of ethyl bromopyruvate (1200 g, 6.15 mol) in methyl alcohol (1.5 L) is then added dropwise over 3 h. The reaction mixture is allowed to reach ambient temperature and stirred an additional 14.5 h. While cooling the reaction mixture via a water bath, a solution of sodium hydroxide (492 g, 12.4 mol) in water (984 mL) is added dropwise over 2.5 h. After stirring at ambient temperature for 15.5 h, the reaction mixture is cooled in an ice water bath, 500 g of ice added, and the resulting mixture is then acidified with concentrated hydrochloric acid (ca 1 L) to pH 1. The reaction mixture is concentrated in vacuo, 1 L of ice is added, and the precipitate filtered, washed with ice water (3×200 mL), and then dried in a vacuum oven at 75° C. to afford 4-oxo-4,5,6,7-tetrahydrobenzofuran-3-carboxylic acid (560 g). m.p. 137–138° C.

2. 4-oxo-4,5,6,7-tetrah droindole-3-carboxylate

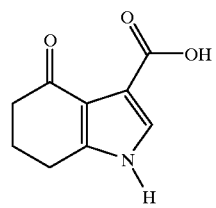

To a stirred mixture of 4-oxo-4,5,6,7-tetrahydrobenzofuran-3-carboxylic acid (640 g, 3.55 mol), potassium carbonate (1.7 kg, 10.65 mol) and cesium carbonate (100 g, 0.32 mol) in N,N-dimethylformamide (9.0 L) is added iodoethane (1250 g, 8.01 mol). The mixture is heated at 60° C. for 2 h. After cooling to ambient temperature, the mixture is filtered, the solid is rinsed with ethyl acetate, and the filtrate concentrated in vacuo. Water (2 L) is added then extracted with ethyl acetate (2×2 L); the combined organic extracts are washed with brine, dried over magnesium sulfate, filtered, and concentrated in vacuo to give ethyl 4-oxo-4,5,6,7-tetrahydrobenzofuran-3-carboxylic acid (642 g). A mixture of this ester (640 g, 3.07 mol) and ammonium acetate (426 g, 5.53 mol) in N,N-dimethylformamide (320 mL) is heated to 100° C. for 2 h. The reaction mixture is concentrated in vacuo, ice water (2.5 L) is added, and extracted with dichloromethane (2×3 L); the combined organic extracts are washed with brine, dried over magnesium sulfate, filtered, and concentrated in vacuo to give ethyl 4-oxo-4,5,6,7-tetrahydroindole-3-carboxylate (357 g). A mixture of this ester (170 g, 0.82 mol) in ethyl alcohol (250 mL) and a solution of sodium hydroxide (165 g, 4.1 mol) in water (1 L) is heated at reflux for 1 h, then cooled in an ice water bath. Concentrated hydrochloric acid (350 mL) is added dropwise, the precipitate collected by filtration, rinsed with ice water (3 ×), and dried in a vacuum oven at 75° C. to afford 4-oxo-4,5,6,7-tetrahydroindole-3-carboxylate (125 g). m.p. 269–270° C.

3. 4-[N-trifluoroacetyl-(methylaminomethyl)aniline

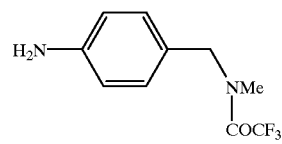

A solution of p-nitrobenzylbromide (5.40 g, 25 mmol) in acetonitrile (60 ml) is added dropwise to a stirred solution of aqueous methylamine (65 mL, 40 wt. %, 0.75 mol) in acetonitrile (50 mL) at 0°. After stirring an additional 15 minutes, the solution is poured into brine and extracted 2× with dichloromethane. The combined organic layers are washed with brine, dried over sodium sulfate, filtered, and concentrated in vacuo to give 4-(methylaminomethyl) nitrobenzene (4.04 g).

A solution of trifluoracetic anhydride (4.46 mL, 31.6 mmol) in dichloromethane (10 mL) is added dropwise to a stirred solution of 4-(methylaminomethyl)nitrobenzene (4.04 g, 24.3 mmol) and pyridine (2.16 mL, 26.7 mmol) in dichloromethane (25 mL) at 0°. After stirring an additional 30 minutes, the solution is poured into aqueous 3.6N hydrochloric acid and extracted with dichloromethane. The organic layer is washed with brine, dried over sodium sulfate, filtered, and concentrated in vacuo to give 4-[N-trifluoroacetyl-(methylaminomethyl)]nitrobenzene (6.55 g).

Crude 4-[N-trifluoroacetyl-(methylaminomethyl)]nitrobenzene (6.55 g) is dissolved in ethyl alcohol (75 mL), added to 10% Pd/C (655 mg) in a Parr bottle and shaken under Hydrogen (50 PSI) for 4 hours. The mixture is filtered through Celite and concentrated in vacuo to give 4-[N-trifluoroacetyl-(methylaminomethyl)aniline (5.75 g).

The 3-aminoalkylanilines are prepared in a similar fashion according to the procedure generally set forth in part (1) of Scheme II above.

4. 4-amino-(N-trifluoroacetyl-2-methylaminoethoxy)benzene

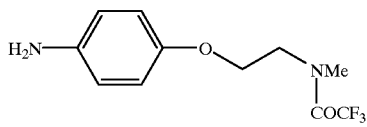

A mixture of p-nitrophenol (1.39 g, 10 mmol), 2-chloroethoxytrimethylsilane (3.2 ml, 20 mmol), potassium carbonate (4.15 g, 30 mmol), cesium carbonate (163 mg, 0.5 mmol), and sodium iodide (149 mg, 1 mmol) in N,N-dimethylformamide (10 ml) is heated at 75° for 19.5 hours. After cooling to ambient temperature, the mixture is diluted with ethyl acetate and filtered. The filtrate is washed with saturated aqueous sodium bicarbonate, then washed 2× with water, dried over magnesium sulfate, filtered, concentrated in vacuo, and purified on Silica gel (1:1 ethyl acetate/hexanes) to give 4-nitro-(2-Hydroxyethoxy)benzene (1.25 g).

4-Nitro-(2-Hydroxyethoxy)benzene (1.13 g, 6.2 mmol) in thionyl chloride (10 mL) is heated at reflux for 3 hours then concentrated in vacuo. After cooling the residue in an ice water bath, saturated aqueous sodium bicarbonate is added and the precipitate collected, rinsed with water, and dried to give 4-nitro-(2-chloroethoxy)benzene (909 mg).

A mixture of 4-nitro-(2-chloroethoxy)benzene (781 mg, 3.9 mmol) and aqueous methylamine (15 mL, 40 wt. %) in isopropyl alcohol (15 mL) is heated in a sealed tube at 100° for 4 hours. After cooling in an ice water bath, the mixtured is poured into brine and extracted 2× with dichloromethane, dried over sodium sulfate, filtered, and concentrated in vacuo to give 4-nitro-(2-methylaminoethoxy)benzene (697 mg).

To a solution of 4-nitro-(2-methylaminoethoxy)benzene (766 mg, 3.9 mmol) and pyridine (0.35 mL, 4.29 mmol) in dichloromethane (5 mL) at 0° C. is added dropwise trifluoroacetic anhydride (0.72 mL, 5.08 mmol). After stirring at 0° C. for 3.5 hours, the mixture is poured into aqueous 1.2 N hydrochloric acid and extracted with dichloromethane. The organic layer is washed with saturated aqueous sodium bicarbonate then brine, dried over sodium sulfate, filtered, and concentrated in vacuo to give 4-nitro-(N-trifluoroacetyl-2-methylaminoethoxy)benzene (1.06 g). Treatment of this nitro compound with 10% Palladium on carbon in ethyl alcohol (18 mL) in a Parr bottle under Hydrogen (55 PSI) for 2.25 hours affords $^4$-amino-(N-trifluoroacetyl-2-methylaminoethoxy)benzene (709 mg).

EXAMPLE 2

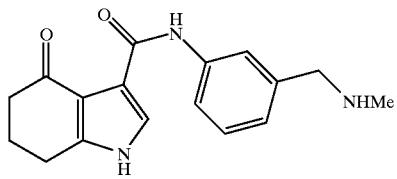

To a stirred solution of 4-oxo-4,5,6,7-tetrahydro-1H-indole-3-carboxylic acid (100 mg, 0.6 mmol) and triethylamine (0.15 mL, 1.1 mmol) in N,N-dimethylformamide (5 mL) at 0° C. is added ethyl chloroformate (0.1 mL, 1.1 mmol). After stirring an additional 1 hour, 3-(N-trifluoroacetyl-(methylaminomethyl)aniline (0.3 g, 1.3 mmol) is added. The reaction mixture is stirrred for 4 hours, then poured into saturated aqueous ammonium chloride and extracted 2× with ethyl acetate. The combined organic layers are washed sequentially with brine, aqueous 2N hydrochloric acid, then brine, dried over sodium sulfate, filtered, and concentrated in vacuo. To the residue is added 15% aqueous potassium bicarbonate (5 mL) and methyl alcohol (3 mL), then heated at reflux for 3 hours. After cooling, the reaction mixture is extracted with ethyl acetate, the organic layer dried over sodium sulfate, filtered, and concentrated in vacuo to give N-[3-(methylaminomethyl)phenyl]-4-oxo-4,5,6,7-tetrahydro-1H-indole-3-carboxamide; (Compound 1) m.p. 130–132° C.

EXAMPLE 3

The following compounds are prepared essentially according to the procedures described in Examples 1–5:

(a) N-[3-(Methylaminomethyl)phenyl]-4-oxo-4,5,6,7-tetrahydro-1H-indole-3-carboxamide (Compound 1); mp 130–132° C.

(b) N-[4-(Hydroxyethoxy)phenyl]-4-oxo-4,5,6,7-tetrahydro-1H-indole-3-carboxamide (Compound 16); mp 245–247° C.

(c) N-[4-(Methoxyethoxy)phenyl]-4-oxo- 4,5,6,7-tetrahydro-1H-indole-3-carboxamide (Compound 2).

(d) N-[-4-(3-Methylaminoethoxy)phenyl]-4-oxo-4,5,6,7-tetrahydro-1H-indole-3-carboxamide (Compound 17); mp 233–236° C.

(e) N-[4-(Methoxymethyl)phenyl]-4-oxo-4,5,6,7-tetrahydro-1H-indole-3-carboxamide (Compound 18); mp 164–165° C.

(f) N-[4-(Aminomethyl)phenyl]-4-oxo-4,5,6,7-tetrahydro-1H-indole-3-carboxamide (Compound 6); mp >200° C. (d).

(g) N-[4-(Methylaminomethyl)phenyl]-4-oxo-4,5,6,7-tetrahydro-1H-indole-3-carboxamide (Compound 19); mp 217–219° C.

(h) N-[2-Fluoro-4-(methylaminomethyl)phenyl]-4-oxo-4,5,6,7-tetrahydro-1H-indole-3-carboxamide (Compound 3); mp 186–188° C.

(i) N-{4-[N-acetyl-(methylaminomethyl)phenyl])}-4-oxo-4,5,6,7-tetrahydro-1H-indole-3-carboxamide (Compound 20); mp 204–206° C.

(j) N-[4-(Ethylaminomethyl)phenyl]-4-oxo-4,5,6,7-tetrahydro-1H-indole-3-carboxamide (Compound 21); mp 194–195° C.

(k) N-[4-(Isopropylaminomethyl)phenyl]-4-oxo-4,5,6,7-tetrahydro-1H-indole-3-carboxamide (Compound 22); mp 164–166° C.

(l) N-[4-(Cyclopropylaminomethyl)phenyl]-4-oxo-4,5,6,7-tetrahydro-1H-indole-3-carboxamide (Compound 5); mp 171–173° C.

(m) N-[4-(Dimethylaminomethyl)phenyl]-4-oxo-4,5,6,7-tetrahydro-1H-indole-3-carboxamide (Compound 23); mp 216–218° C.

(n) N-[4-(2-Aminoethyl)phenyl]-4-oxo-4,5,6,7-tetrahydro-1H-ndole-3-carboxamide (Compound 24); mp 85–90° C.

(o) N-[4-(2-Methylaminoethyl)phenyl]-4-oxo-4,5,6,7-tetrahydro-1H-indole-3-carboxamide (Compound 4); mp 197–200° C.

(p) N-[4-(Methoxymethyl)phenyl]-4-oxo-5,5-dimethyl-4,5,6,7-tetrahydro-1H-indole-3-carboxamide (Compound 25).

(q) N-[4-(Methylaminomethyl)phenyl-4-oxo-1,4,5,6,7,8-hexahydro-cyclohepta[b]pyrrole-3-carboxamide (Compound 7); mp 173–175° C.

(r) N-{4-[N-acetyl-(methylaminomethyl)phenyl]}-4-oxo-6-methyl-4,5,6,7-tetrahydro-1H-indole-3-carboxamide (Compound 26); mp 159–161° C.

(s) N-[4-(Methylaminomethyl)phenyl]-4-oxo-6-methyl-4,5,6,7-tetrahydro-1H-indole-3-carboxamide (Compound 27); mp 217–219° C.

(t) N-[4-(Hydroxymethyl)phenyl]-4-oxo-6-methyl-4,5,6,7-tetrahydro-1H-indole-3-carboxamide (Compound 28); mp 260-262° C.

(u) N-[4-(2-Hydroxyethoxy)phenyl]-4-oxo-6-methyl-4,5,6,7-tetrahydro-1H-indole-3-carboxamide (Compound 9); mp 245–247° C.

(v) N-[3-(Methylaminomethyl)phenyl]-4-oxo-6-methyl-4,5,6,7-tetraydro-1H-indole-3-carboxamide (Compound 29); mp 172–174° C.

(w) N-[4-(2-Hydroxyethoxy)phenyl]-4-oxo-6,6-dimethyl-4,5,6,7-tetrahydro-1H-indole-3-carboxamide (Compound 30); mp 268–270° C.

(x) N-[3-(Hydroxymethyl)phenyl]-4-oxo-6,6-dimethyl-4,5,6,7-tetrahydro-1H-indole-3-carboxamide (Compound 8); mp 233–235° C.

(y) N-[4-(Hydroxymethyl)phenyl]-4-oxo-6,6-dimethyl-4,5,6,7-tetrahydro-1H-indole-3-carboxamide (Compound 31); mp 245–247° C.

(z) N-[4-(Methylaminomethyl)phenyl]-4-oxo-6,6-dimethyl-4,5,6,7-tetrahydro-1H-indole-3-carboxamide (Compound 32); mp 230–232° C.

(aa) N-(1,3-Benzodioxol-5-yl)-4-oxo-4,5,6,7-tetrahydro-1H-indole-3-carboxamide (Compound 10); mp 248–249° C.

(bb) N-(2,3-Dihydro-1,4-benzodioxin-6-yl)-4-oxo-4,5,6,7-tetrahydro-1H-indole-3-carboxamide (Compound 11); mp 254–256° C.

(cc) N-(3,4-Dihydro-2H-1,4-benzoxazin-6-yl)-4-oxo-4,5,6,7-tetrahydro-1H-indole-3-carboxamide (Compound 33); mp 216° C.

(dd) N-(2,2-Dimethyl-1,3-benzodioxol-5-yl)-4-oxo-4,5,6,7-tetrahydro-1H-indole-3-carboxamide (Compound 34).

(ee) N-(2,3-Dihydro-1H-indol-5-yl)4-oxo-4,5,6,7-tetrahydro-1H-indole-3-carboxamide (Compound 35); mp 283–286° C.

(ff) N-(2,3-Dihydro-1H-indol-6-yl)-4-oxo-4,5,6,7-tetrahydro-1H-indole-3-carboxamide (Compound 13); mp 322–323° C.

(gg) N-(1,3-Benzodioxol-5-yl)-4-oxo-5,5-dimethyl-4,5,6,7-tetrahydro-1H-indole-3-carboxamide (Compound 36).

(hh) N-(2,3-Dihydro-1,4-benzodioxin-6-yl)-4-oxo-5,5-dimethyl-4,5,6,7-tetrahydro-1H-indole-3-carboxamide (Compound 37); mp 241–243° C.

(ii) N-(4H-1,3-Benzodioxin-7-yl)-4-oxo-5,5-dimethyl-4,5,6,7-tetrahydro-1H-indole-3-carboxamide (Compound 38); mp 251–252° C.

(jj) N-(1,3-Benzodioxol-5-yl)-4-oxo-1,4,5,6,7,8-hexahydro-cyclohepta[b]pyrrole-3-carboxamide (Compound 39); mp 210–212° C.

(kk) N-(2,3-Dihydro-1,4-benzodioxin-6-yl)-4-oxo-1,4,5,6,7,8-hexahydro-cyclohepta[b]pyrrole-3-carboxamide (Compound 12); mp 222–223° C.

(ll) N-(2,2-Dimethyl-1,3-benzodioxol-5-yl)-4-oxo-6-methyl-4,5,6,7-tetrahydro-1H-indole-3-carboxamide (Compound 40); mp 155–157° C.

(mm) N-(1,3-Benzodioxol-5-yl)-4-oxo-6-methyl-4,5,6,7-tetrahydro-1H-indole-3-carboxamide (Compound 41); mp 297–299° C.

(nn) N-(2,3-Dihydro-1,4-benzodioxin-6-yl)-4-oxo-6-methyl-4,5,6,7-tetrahydro-1H-indole-3-carboxamide (Compound 42); mp 290–292° C.

(oo) N-(1,3-Benzodioxol-5-yl)-4-oxo-6,6-dimethyl-4,5,6,7-tetrahydro-1H-indole-3-carboxamide (Compound 43); mp 245–246° C.

(pp) N-(2,3-Dihydro-1,4-benzodioxin-6-yl)-4-oxo-6,6-dimethyl-4,5,6,7-tetrahydro-1H-indole-3-carboxamide (Compound 44).

(qq) N-(4H-1,3-Benzodioxin-7-yl)-4-oxo-6,6-dimethyl-4,5,6,7-tetrahydro-1H-indole-3-carboxamide (Compound 45); mp 234–236° C.

(rr) N-[(2-Hydroxyethoxy)pyrid-5-yl]-4-oxo-6-methyl-4,5,6,7-tetrahydro-1H-indole-3-carboxamide (Compound 15); mp 221–223° C.

(ss) N-(3,4-Dihydro-2H-1,4-benzoxazin-7-yl)-4-oxo-4,5,6,7-tetrahydro-1H-indole-3-carboxamide (Compound 46).

(tt) N-[3-(2-Pyrrolidinylethoxy)phenyl]-4-oxo-4,5,6,7-tetrahydro-1H-indole-3-carboxamide; [alternate name: (4-oxo(5,6,7-trihydroindol-3-yl))-N-[4-(2-pyrrolidinylethoxy)phenyl]carboxamide] (Compound 47);

(uu) N-[3-(2-Dimethylaminoethoxy)phenyl]-4-oxo-4,5,6,7-tetrahydro-1H-indole-3-carboxamide [alternate name: (4-oxo(5,6,7-trihydroindol-3-yl))-N-[4-(2-Dimethylaminoethoxy)phenyl]carboxamide] (Compound 48);

(vv) N-[3-(2-n-Propylaminoethoxy)phenyl]-4-oxo-4,5,6,7-tetrahydro-1H-indole-3-carboxamide (Compound 49).

(ww) N-[3-(2-n-Butylaminoethoxy)phenyl]-4-oxo-4,5,6,7-tetrahydro-1H-indole-3-carboxamide (Compound 50).

(xx) N-[3-(2-Isobutylaminoethoxy)phenyl]-4-oxo-4,5,6,7-tetrahydro-1H-indole-3-carboxamide (Compound 51) (syrup).

(yy) N-[3-(2-Cyclobutylaminoethoxy)phenyl]-4-oxo-4,5,6,7-tetrahydro-1H-indole-3-carboxarnide (Compound 52).

(zz) N-[3-(2-t-Butylaminoethoxy)phenyl]-4-oxo-4,5,6,7-tetrahydro-1H-indole-3-carboxamide (Compound 53).

(aaa) N-[3-(2-Cyclopropylmethylaminoethoxy)phenyl]-4-oxo-4,5,6,7-tetrahydro-1H-indole-3-carboxamide (Compound 54).

(bbb) N-{3-[2-(4-Methylcyclohexyl)aminoethoxy]phenyl}-4-oxo-4,5,6,7-tetrahydro-1H-indole-3-carboxamide (Compound 55).

(ccc) N-{3-[2-(3-Trifluoromethylbenzylamino)ethoxy]phenyl}-4-oxo-4,5,6,7-tetrahydro-1H-indole-3-carboxamide (Compound 56).

(ddd) N-{3-[3-(3-Trifluoromethylbenzylamino)propoxy]phenyl}-4-oxo-4,5,6,7-tetrahydro-1H-indole-3-carboxamide (Compound 57).

(eee) N-[4-(2-Dimethylaminoethyl)phenyl]-4-oxo-4,5,6,7-tetrahydro-1H-indole-3-carboxamide (Compound 58).

(fff) N-[4-(2-Pyrrolidin-1-ylethyl)phenyl]-4-oxo-4,5,6,7-tetrahydro-1H-indole-3-carboxamide (Compound 59); mp 184–186° C.

(ggg) N-[4-(2-Diisopropylaminoethoxy)phenyl]-4-oxo-4,5,6,7-tetrahydro-1H-indole-3-carboxamide (Compound 60).

(hhh) N-[4-(2-Methylaminoethoxy)phenyl]-4-oxo-4,5,6,7-tetrahydro-1H-indole-3-carboxamide (Compound 61).

(iii) N-[4-(2-Ethylaminoethoxy)phenyl]-4-oxo-4,5,6,7-tetrahydro-1H-indole-3-carboxamide (Compound 62); mp 140–141° C.

(jjj) N-[2-Fluoro-4-(2-ethylaminoethoxy)phenyl]-4-oxo-4,5,6,7-tetrahydro-1H-indole-3-carboxamide (Compound 63).

(kkk) N-[4-(2-n-Propylaminoethoxy)phenyl]-4-oxo-4,5,6,7-tetrahydro-1H-indole-3-carboxamide (Compound 64); mp 130–133° C.

(lll) N-[2-Fluoro-4-(2-n-propylaminoethoxy)phenyl]-4-oxo-4,5,6,7-tetrahydro-1H-indole-3-carboxamide (Compound 65).

(mmm) N-[3-Fluoro-4-(2-n-propylaminoethoxy)phenyl]-4-oxo-4,5,6,7-tetrahydro-1H-indole-3-carboxamide (Compound 66).

(mmm-a) N-[3-Fluoro-4-(2-n-propylaminoethoxy)phenyl]-4-oxo-4,5,6,7-tetrahydro-1H-indole-3-carboxamide hydrochloride (Compound 67); mp 373° C.

(nnn) N-[4-(2-Cyclopropylaminoethoxy)phenyl]-4-oxo-4,5,6,7-tetrahydro-1H-indole-3-carboxamide (Compound 68).

(ooo) N-[4-(2-Isopropylaminoethoxy)phenyl]-4-oxo-4,5,6,7-tetrahydro-1H-indole-3-carboxamide (Compound 69); mp 284–286° C.

(ppp) N-[4-(2-Cyclopropylmethylaminoethoxy)phenyl]-4-oxo-4,5,6,7-tetrahydro-1H-indole-3-carboxamide (Compound 70).

(ppp-a) N-[4-(2-Cyclopropylmethylaminoethoxy)phenyl]-4-oxo-4,5,6,7-tetrahydro-1H-indole-3-carboxamide hemifumarate (Compound 71); mp234–234° C.

(qqq) N-[2-Fluoro-4-(2-Cyclopropylmethylaminoethoxy)phenyl]-4-oxo-4,5,6,7-tetrahydro-1H-indole-3-carboxamide (Compound 72); mp 247–250° C.

(rrr) N-[3-Fluoro-4-(2-Cyclopropylmethylaminoethoxy)phenyl]-4-oxo-4,5,6,7-tetrahydro-1H-indole-3-carboxamide (Compound 73).

(rrr-a) N-[3-Fluoro-4-(2-Cyclopropylmethylaminoethoxy)phenyl]-4-oxo-4,5,6,7-tetrahydro-1H-indole-3-carboxamide tosylate (Compound 74); mp 222° C.

(sss) N-[4-(2-Isobutylaminoethoxy)phenyl]-4-oxo-4,5,6,7-tetrahydro-1H-indole-3-carboxamide (Compound 75); dust.

(ttt) N-[2-Fluoro-4-(2-Isobutylaminoethoxy)phenyl]-4-oxo-4,5,6,7-tetrahydro-1H-indole-3-carboxamide (Compound 76); mp 152–155° C.

(uuu) N-[3-Fluoro-4-(2-Isobutylaminoethoxy)phenyl]-4-oxo-4,5,6,7-tetrahydro-1H-indole-3-carboxamide (Compound 77); mp 147–149° C.

(vvv) N-[4-(2-n-Butylaminoethoxy)phenyl]-4-oxo-4,5,6,7-tetrahydro-1H-indole-3-carboxamide (Compound 78).

(vvv-a) N-[4-(2-n-Butylaminoethoxy)phenyl]-4-oxo-4,5,6,7-tetrahydro-1H-indole-3-carboxamide hydrochloride (Compound 79); mp 187–190° C.

(www) N-[3-Fluoro-4-(2-n-butylaminoethoxy)phenyl]-4-oxo-4,5,6,7-tetrahydro-1H-indole-3-carboxamide (Compound 80).

(xxx) N-[4-(2-t-Butylaminoethoxy)phenyl]-4-oxo-4,5,6,7-tetrahydro-1H-indole-3-carboxamide (Compound 81); mp 290–292° C.

(yyy) N-[3-Fluoro-4-(2-t-butylaminoethoxy)phenyl]-4-oxo-4,5,6,7-tetrahydro-1H-indole-3-carboxamide (Compound 82).

(aaaa) N-[4-(2-adamant-2-ylaminoethoxy)phenyl]-4-oxo-4,5,6,7-tetrahydro-1H-indole-3-carboxamide (Compound 83); mp 144–149° C.

(bbbb) N-{4-[(R)-Pyrrolidin-2-ylmethoxy]phenyl}-4-oxo-4,5,6,7-tetrahydro-1H-indole-3-carboxamide (Compound 84); mp 164–167–170° C.

(cccc) N-{4-[(S)-Pyrrolidin-2-ylmethoxy]phenyl}-4-oxo-4,5,6,7-tetrahydro-1H-indole-3-carboxamide (Compound 85); mp 165–167° C.

(dddd) N-[4-(Piperidin-3-ylmethoxy)phenyl]-4-oxo-4,5,6,7-tetrahydro-1H-indole-3-carboxamide (Compound 86).

(dddd-a) N-[4-(Piperidin-3-ylmethoxy)phenyl]-4-oxo-4,5,6,7-tetrahydro-1H-indole-3-carboxamide hydrochloride (Compound 87); mp 196–199° C.

(eeee) N-[4-(2-Dimethylaminoethoxy)phenyl]-4-oxo-4,5,6,7-tetrahydro-1H-indole-3-carboxamide (Compound 88); mp 201° C.

(ffff) N-[3-Fluoro-4-(2-dimethylaminoethoxy)phenyl]-4-oxo-4,5,6,7-tetrahydro-1H-indole-3-carboxamide (Compound 89); mp 203° C.

(gggg) N-[4-(2-Pyrrolidin-1-ylethoxy)phenyl]-4-oxo-4,5,6,7-tetrahydro-1H-indole-3-carboxamide (Compound 90); mp 164–168° C.

(hhhh) N-[4-(2-Imidaz-1-ylethoxy)phenyl]-4-oxo-4,5,6,7-tetrahydro-1H-indole-3-carboxamide (Compound 91); mp 226–230° C.

(iiii) N-[3-Fluoro-4-(2-moropholin-1-ylethoxy)phenyl]-4-oxo-4,5,6,7-tetrahydro-1H-indole-3-carboxamide (Compound 92); mp 200° C.

(jjjj) N-[3-Fluoro-4-(2-pyrrolidin-1-ylethoxy)phenyl]-4-oxo-4,5,6,7-tetrahydro-1H-indole-3-carboxamide (Compound 93).

(kkkk) N-[4-(2-Piperidin-2-ylethoxy)phenyl]-4-oxo-4,5,6,7-tetrahydro-1H-indole-3-carboxamide (Compound 94); mp 281–285° C.

(llll) N-{4-[3-(2,2,2,-Trifluoroethyl)aminopropoxy]phenyl}-4-oxo-4,5,6,7-tetrahydro-1H-indole-3-carboxamide (Compound 95).

(mmmm) N-[4-(3-Isopropylaminopropoxy)phenyl]-4-oxo-4,5,6,7-tetrahydro-1H-indole-3-carboxamide (Compound 96).

(nnnn) N-{4-[3-(2-Methylpropyl)aminopropoxy]phenyl}-4-oxo-4,5,6,7-tetrahydro-1H-indole-3-carboxamide (Compound 97).

(oooo) N-[4-(3-Isobutylaminopropoxy)phenyl]-4-oxo-4,5,6,7-tetrahydro-1H-indole-3-carboxamide (Compound 98).

(pppp) N-[4-(3-Cyclopropylmethylaminopropoxy)phenyl]-4-oxo-4,5,6,7-tetrahydro-1H-indole-3-carboxamide (Compound 99).

(qqqq) N-{4-[3-(3-Ethylpropyl)aminopropoxy]phenyl}-4-oxo-4,5,6,7-tetrahydro-1H-indole-3-carboxamide (Compound 100).

(rrrr) N-[4-(3-Cyclopentylaminopropoxy)phenyl]-4-oxo-4,5,6,7-tetrahydro-1H-indole-3-carboxamide (Compound 101).

(ssss) N-{4-[3-(N-Cyclopropylmethyl,N-propyl)aminopropoxy]phenyl}-4-oxo-4,5,6,7-tetrahydro-1H-indole-3-carboxamide (Compound 102).

(tttt) N-[4-(2-Methylaminoethoxy)pyrid-3-yl]-4-oxo-4,5,6,7-tetrahydro-1H-indole-3-carboxamide (Compound 103).

(uuuu) N-[4-(2-Ethylaminoethoxy)pyrid-3-yl]-4-oxo-4,5,6,7-tetrahydro-1H-indole-3-carboxamide (Compound 104).

(uuuu-a) N-[4-(2-Ethylaminoethoxy)pyrid-3-yl]-4-oxo-4,5,6,7-tetrahydro-1H-indole-3-carboxamide hydrochloride (Compound 105); mp 178–180° C.

(vvvv) N-[4-(2-n-Propylaminoethoxy)pyrid-3-yl]-4-oxo-4,5,6,7-tetrahydro-1H-indole-3-carboxamide (Compound 106).

(vvvv-a) N-[4-(2-n-Propylaminoethoxy)pyrid-3-yl]-4-oxo-4,5,6,7-tetrahydro-1H-indole-3-carboxamide hydrochloride (Compound 107); mp 177–178° C.

(wwww) N-[4-(2-Isopropylaminoethoxy)pyrid-3-yl]-4-oxo-4,5,6,7-tetrahydro-1H-indole-3-carboxamide (Compound 108).

(wwww-a) N-[4-(2-Isopropylaminoethoxy)pyrid-3-yl]-4-oxo4,5,6,7-tetrahydro-1H-indole-3-carboxamide hydrochloride (Compound 109); mp 167–169° C.

(xxxx) N-[4-(2-n-Butylaminoethoxy)pyrid-3-yl]-4-oxo-4,5,6,7-tetrahydro-1H-indole-3-carboxamide (Compound 110).

(xxxx-a) N-[4-(2-n-Butylaminoethoxy)pyrid-3-yl]-4-oxo-4,5,6,7-tetrahydro-1H-indole-3-carboxamide hydrochloride (Compound 111); mp 157–159° C.

(yyyy) N-[4-(2-t-Butylaminoethoxy)pyrid-3-yl]-4-oxo-4,5,6,7-tetrahydro-1H-indole-3-carboxamide (Compound 112); mp 274–278° C.

(zzzz) N-[4-(2-Benzylaminoethoxy)pyrid-3-yl]-4-oxo-4,5,6,7-tetrahydro-1H-indole-3-carboxamide (Compound 113)

(zzzz-a) N-[4-(2-Benzylaminoethoxy)pyrid-3-yl]-4-oxo-4,5,6,7-tetrahydro-1H-indole-3-carboxamide hydrochloride (Compound 114); mp 143–145° C.

(aaaaa-a) N-[4-(Pyrid-3-ylmethoxy)pyrid-3-yl]-4-oxo-4,5,6,7-tetrahydro-1H-indole-3-carboxamide (Compound 115).

(aaaaa) N-[4-(Pyrid-3-ylmethoxy)pyrid-3-yl]-4-oxo-4,5,6,7-tetrahydro-1H-indole-3-carboxamide hydrochloride (Compound 116); mp 276–277° C.

(bbbbb) N-[4-(Pyrid-4-ylmethoxy)pyrid-3-yl]-4-oxo-4,5,6,7-tetrahydro-1H-indole-3-carboxamide (Compound 117).

(bbbbb-a) N-[4-(Pyrid-4ylmethoxy)pyrid-3-yl]-4-oxo-4,5,6,7-tetrahydro-1H-indole-3-carboxamide hydrochloride (Compound 118); mp 293° C.

(ccccc) N-{4-[(R)-Pyrrolidn-2-ylmethoxy]pyrid-3-yl}-4-oxo-4,5,6,7-tetrahydro-1H-indole-3-carboxamide (Compound 119); mp 195–198° C.

(ccccc-a) N-{4-[(R)-Pyrrolidn-2-ylmethoxy]pyrid-3-yl}-4-oxo-4,5,6,7-tetrahydro-1H-indole-3-carboxamide hydrochloride (Compound 120); mp 289–291° C.

(ddddd) N-{4-[(S)-Pyrrolidn-2-ylmethoxy]pyrid-3-yl}-4-oxo-4,5,6,7-tetrahydro-1H-indole-3-carboxamide (Compound 121); mp 138–141° C.

(eeeee) N-[4-(2-Dimethylaminoethoxy)pyrid-3-yl]-4-oxo-4,5,6,7-tetrahydro-1H-indole-3-carboxamide (Compound 122); mp 163–166° C.

(fffff) N-[4-(3-Dimethylaminopropoxy)pyrid-3-yl]-4-oxo-4,5,6,7-tetrahydro-1H-indole-3-carboxamide (Compound 123); mp 247° C.

(ggggg) N-[4-(2-Pyrrolidin-1-ylethoxy)pyrid-3-yl]-4-oxo-4,5,6,7-tetrahydro-1H-indole-3-carboxamide (Compound 124)

(ggggg-a) N-[4-(2-Pyrrolidin-1-ylethoxy)pyrid-3-yl]-4-oxo-4,5,6,7-tetrahydro-1H-indole-3-carboxamide hydrochloride (Compound 125); mp 188–245° C. (d).

(hhhhh) N-[4-(2-Dimethylaminoethoxy)pyrid-3-yl]-4-oxo-4,5,6,7-tetrahydro-1H-indole-3-carboxamide (Compound 126).

(iiiii) N-{4-[2-(4-Methyl-piperazin-1-yl)ethoxy]pyrid-3-yl}-4-oxo-4,5,6,7-tetrahydro-1H-indole-3-carboxamide (Compound 127).

(jjjjj) N-{4-[2-Morpholin-1-ylethoxy]pyrid-3-yl}-4-oxo-4,5,6,7-tetrahydro-1H-indole-3-carboxamide (Compound 128).

(kkkkk) N-{4-[2-Piperidin-1-ylethoxy]pyrid-3-yl}-4-oxo-4,5,6,7-tetrahydro-1H-indole-3-carboxamide hydrochloride (Compound 129).

(kkkkk-a) N-{4-[2-Piperidin-1-ylethoxy]pyrid-3-yl}-4-oxo-4,5,6,7-tetrahydro-1H-indole-3-carboxamide hydrochloride (Compound 130); mp 208–211° C.

(lllll) N-{4-[(1-Methyl-pyrrolidin-3-yl)methoxy]pyrid-3-yl}-4-oxo-4,5,6,7-tetrahydro-1H-indole-3-carboxamide (Compound 131); mp 209–211° C.

(mmmmm) N-{4-[(1-Ethyl-pyrrolidin-3-yl)methoxy]pyrid-3-yl}-4-oxo-4,5,6,7-tetrahydro-1H-indole-3-carboxamide (Compound 132).

(nnnnnn) N-{4-[2-(1-Methyl-pyrrolidin-2-yl)ethoxy]pyrid-3-yl}-4-oxo-4,5,6,7-tetrahydro-1H-indole-3-carboxamide (Compound 133).

(ooooo) N-{4-[2-(1-Methyl-pyrrolidin-2-yl)ethoxy]pyrid-3-yl}-4-oxo-4,5,6,7-tetrahydro-1H-indole-3-carboxamide hydrate (Compound 134).

(ppppp) N-[4-(3-n-Propylaminopropoxy)pyrid-3-yl]-4-oxo-4,5,6,7-tetrahydro-1H-indole-3-carboxamide (Compound 135).

(qqqqq) N-[4-(3-Cyclopropylmethylaminopropoxy)pyrid-3-yl]-4-oxo-4,5,6,7-tetrahydro-1H-indole-3-carboxamide (Compound 136).

(rrrrr) N-{4-[3-(2-Ethylbutyl)aminopropoxy]pyrid-3-yl}-4-oxo-4,5,6,7-tetrahydro-1H-indole-3-carboxamide (Compound 137).

(sssss) N-[4-(3-Cyclohexylaminopropoxy)pyrid-3-yl]-4-oxo-4,5,6,7-tetrahydro-1H-indole-3-carboxamide (Compound 138).

(ttttt) N-[4-(3-Cyclohexylmethylaminopropoxy)pyrid-3-yl]-4-oxo-4,5,6,7-tetrahydro-1H-indole-3-carboxamide (Compound 139).

(uuuuu) N-{4-[3-(Pyrid-4-ylmethyl)aminopropoxy]pyrid-3-yl}-4-oxo-4,5,6,7-tetrahydro-1H-indole-3-carboxamide (Compound 140).

(vvvvv) N-[4-(2-Pyrrolidin-1-ylethoxy)pyrid-3-yl]-4-oxo-4,5,6,7-tetrahydro-1H-indole-3-carboxamide (Compound 141); mp 148–150° C.

(wwwww) N-[4-(3-Di-n-propylaminopropoxy)pyrid-3-yl]-4-oxo-4,5,6,7-tetrahydro-1H-indole-3-carboxamide (Compound 142).

(xxxxx) N-{4-[3-Di(c-propylmethyl)aminopropoxy]pyrid-3-yl}-4-oxo-4,5,6,7-tetrahydro-1H-indole-3-carboxamide (Compound 143).

(yyyyy) N-{4-[3-Di(2-ethylbutyl)aminopropoxy]pyrid-3-yl}-4-oxo-4,5,6,7-tetrahydro-1H-indole-3-carboxamide (Compound 144).

(zzzzz) N-{4-[3-Di(pyrid-4-ylmethyl)aminopropoxy]pyrid-3-yl}-4-oxo-4,5,6,7-tetrahydro-1H-indole-3-carboxamide (Compound 145).

(aaaaaa) N-{4-[2-(2-Pyrrolidin-1-ylethoxy)ethoxy]prid-3-yl}-4-oxo-4,5,6,7-tetrahydro-1H-indole-3-carboxamide (Compound 146).

(bbbbbb) N-{4-[2-(2,2-Dimethylaminoethylamino)-2-oxoethyl]phenyl}-4-oxo -4,5,6,7-tetrahydro-1H-indole-3-carboxamide (Compound 147).

(cccccc) N-{4-[2-(4-Methylaminopiperizin-1yl)-2-oxoethyl]phenyl}-4-oxo-4,5,6,7-tetrahydro-1H-indole-3-carboxamide (Compound 148); oil.

(dddddd) N-{4-[7-azabicyclo(2,2,1)hept-2-yloxy]phenyl}-4-oxo-1,4,5,6,7,8-hexahydro-cyclohepta[b]pyrrole-3-carboxamide (Compound 149).

(eeeeee) N-[3-(2-Diethylaminoethoxy)phenyl]-4-oxo-1,4,5,6,7,8-hexahydro-cyclohepta[b]pyrrole-3-carboxamide (Compound 150).

(ffffff) N-[3-(2-Pyrrolidin-1-ylethoxy)phenyl]-4-oxo-1,4,5,6,7,8-hexahydro-cyclohepta[b]pyrrole-3-carboxamide (Compound 151).

(gggggg) N-[3-(2-Di-Isopropylaminoethoxy)phenyl]-4-oxo-1,4,5,6,7,8-hexahydro-cyclohepta[b]pyrrole-3-carboxamide (Compound 152).

(hhhhhh) N-[3-(2-n-Propylaminoethoxy)phenyl]-4-oxo-1,4,5,6,7,8-hexahydro-cyclohepta[b]pyrrole-3-carboxamide (Compound 153).

(iiiiii) N-[3-(2-n-Butylaminoethoxy)phenyl]-4-oxo-1,4,5,6,7,8-hexahydro-cyclohepta[b]pyrrole -3-carboxamide (Compound 154).

(jjjjjj) N-[3-(Methylaminopropoxy)phenyl]-4-oxo-1,4,5,6,7,8-hexahydro-cyclohepta[b]pyrrole-3-carboxamide (Compound 155).

(kkkkkk) N-{3-[3-(N-Ethyl,N-Methyl)aminopropoxy]phenyl}-4-oxo-1,4,5,6,7,8-hexahydro-cyclohepta[b]pyrrole-3-carboxamide (Compound 156).

(llllll) N-{3-[3-(N-Cyclopropylmethyl,N-n-propyl)aminopropoxy]phenyl}-4-oxo-1,4,5,6,7,8-hexahydro-cyclohepta[b]pyrrole-3-carboxamide (Compound 157).

(mmmmmm) N-[3-(Azeditinylpropoxy)phenyl]-4-oxo-1,4,5,6,7,8-hexahydro-cyclohepta[b]pyrrole-3-carboxamide (Compound 158).

(nnnnnn) N-[3-(3-Ethylaminopropoxy)phenyl]-4-oxo-1,4,5,6,7,8-hexahydro-cyclohepta[b]pyrrole-3-carboxamide (Compound 159).

(oooooo) N-{3-{3-(2,2,2-Trifluoroethyl)aminopropoxy]phenyl}-4-oxo- 1,4,5,6,7,8-hexahydro-cyclohepta[b]pyrrole-3-carboxamide (Compound 160).

(pppppp) N-[3-(3-n-Proplaminopropoxy)phenyl]-4-oxo-1,4,5,6,7,8-hexahydro-cyclohepta[b]pyrrole-3-carboxamide (Compound 161).

(rrrrrr) N-[3-(3-Isopropylaminopropoxy)phenyl]-4-oxo-1,4,5,6,7,8-hexahydro-cyclohepta[b]pyrrole-3-carboxamide (Compound 163).

(ssssss) N-[3-(3-Cyclopropylaminopropoxy)phenyl]-4-oxo-1,4,5,6,7,8-hexahydro-cyclohepta[b]pyrrole-3-carboxamide (Compound 164).

(tttttt) N-[3-(3-Cyclopropylmethylaminopropoxy)phenyl]-4-oxo-1,4,5,6,7,8-hexahydro-cyclohepta[b]pyrrole-3-carboxamide (Compound 165).

(uuuuuu) N-[3-(3-Cyclobutylaminopropoxy)phenyl]-4-oxo-1,4,5,6,7,8-hexahydro-cyclohepta[b]pyrrole-3-carboxamide (Compound 166).

(vvvvvv) N-[3-(3-Cyclohexylaminopropoxy)phenyl]-4-oxo-1,4,5,6,7,8-hexahydro-cyclohepta[b]pyrrole-3-carboxamide (Compound 167).

(wwwwww) N-{3-[3-(3-Ethylpropyl)aminopropoxy]phenyl}-4-oxo-1,4,5,6,7,8-hexahydro-cyclohepta[b]pyrrole-3-carboxamide (Compound 168).

(xxxxxx) N-{3-[3-(2-Methylpropyl)aminopropoxy]phenyl}-4-oxo-1,4,5,6,7,8-hexahydro-cyclohepta[b]pyrrole-3-carboxamide (Compound 169).

(yyyyyy) N-[3-(3-Isobutylaminopropoxy)phenyl]-4-oxo-1,4,5,6,7,8-hexahydro-cyclohepta[b]pyrrole-3-carboxamide (Compound 170).

(zzzzzz) N-[3-(3-t-Butylaminopropoxy)phenyl]-4-oxo-1,4,5,6,7,8-hexahydro-cyclohepta[b]pyrrole-3-carboxamide (Compound 171).

(aaaaaaa) N-{3-[3-(2-Methylbutyl)aminopropoxy]phenyl}-4-oxo-1,4,5,6,7,8-hexahydro-cyclohepta[b]pyrrole-3-carboxamide (Compound 172).

(bbbbbbb) N-[3-(3-Isoamylaminopropoxy)phenyl]-4-oxo-1,4,5,6,7,8-hexahydro-cyclohepta[b]pyrrole-3-carboxamide (Compound 173).

(ccccccc) N-{3-[3-(4-Methylpentyl)aminopropoxy]phenyl}-4-oxo-1,4,5,6,7,8-hexahydro-cyclohepta[b]pyrrole-3-carboxamide (Compound 174).

(ddddddd) N-{3-[3-(1,1 -Dimethylpropyl)aminopropoxy]phenyl}-4-oxo-1,4,5,6,7,8-hexahydro-cyclohepta[b]pyrrole-3-carboxamide (Compound 175).

(eeeeeee) N-{3-[3-(3,3,-Dimethylbutyl)aminopropoxy]phenyl}-4-oxo-1,4,5,6,7,8-hexahydro-cyclohepta[b]pyrrole-3-carboxamide (Compound 176).

(fffffff) N-{3-[3-(2,4-Dimethylpent-3-yl)aminopropoxy]phenyl}-4-oxo-1,4,5,6,7,8-hexahydro-cyclohepta[b]pyrrole-3-carboxamide (Compound 177).

(ggggggg) N-{3-[3-(4-Methylcyclohexyl)aminopropoxy]phenyl}-4-oxo-1,4,5,6,7,8-hexahydro-cyclohepta[b]pyrrole-3-carboxamide (Compound 178).

(hhhhhhh) N-{3-[3-(4-t-Butylcyclohexyl)aminopropoxy]phenyl}-4-oxo-1,4,5,6,7,8-hexahydro-cyclohepta[b]pyrrole-3-carboxamide (Compound 179).

(iiiiiii) N-{3-[3-(2,6-Dimethylcyclohexyl)aminopropoxy]phenyl}-4-oxo-1,4,5,6,7,8-hexahydro-cyclohepta[b]pyrrole-3-carboxamide (Compound 180).

(jjjjjj) N-{3-[3-(1-Phenylethyl)aminopropoxy]phenyl}-4-oxo-1,4,5,6,7,8-hexahydro-cyclohepta[b]pyrrole-3-carboxamide (Compound 181).

(kkkkkkk) N-[3-(3-Norborn-2-ylaminopropoxy)phenyl]-4-oxo-1,4,5,6,7,8-hexahydro-cyclohepta[b]pyrrole-3-carboxamide (Compound 182).

(lllllll) N-[3-(3-Adamant-1-ylaminopropoxy)phenyl]4-oxo-1,4,5,6,7,8-hexahydro-cyclohepta[b]pyrrole-3-carboxamide (Compound 183); mp 175–176° C.

(mmmmmmm) N-[3-(3-Norborn-2-ylmethylaminopropoxy)phenyl]-4-oxo-1,4,5,6,7,8-hexahydro-cyclohepta[b]pyrrole-3-carboxamide (Compound 184).

(nnnnnnn) N-[3-(3-Adamant-2-ylaminopropoxy)phenyl]-4-oxo-1,4,5,6,7,8-hexahydro-cyclohepta[b]pyrrole-3-carboxamide (Compound 185).

(ooooooo) N-[4-(2-Ethylaminoethoxy)phenyl]-4-oxo-1,4,5,6,7,8-hexahydro-cyclohepta[b]pyrrole-3-carboxamide (Compound 186).

(ooooooo-a) N-[4-(2-Ethylaminoethoxy)phenyl]-4-oxo-1,4,5,6,7,8-hexahydro-cyclohepta[b]pyrrole-3-carboxamide hydrochloride (Compound 187); mp 227–228° C.

(ppppppp) N-[2-Fluoro-4-(2-Ethylaminoethoxy)phenyl]-4-oxo-1,4,5,6,7,8-hexahydro-cyclohepta[b]pyrrole-3-carboxamide (Compound 188).

(qqqqqqq) N-[4-(2-n-Propylaminoethoxy)phenyl]-4-oxo-1,4,5,6,7,8-hexahydro-cyclohepta[b]pyrrole-3-carboxamide (Compound 189).

(rrrrrrr) N-[4-(2-Cyclopropylaminoethoxy)phenyl]-4-oxo- 1,4,5,6,7,8-hexahydro-cyclohepta[b]pyrrole-3-carboxamide (Compound 190).

(sssssss) N-4-(2-n-Butylaminoethoxy)phenyl]-4-oxo-1,4,5,6,7,8-hexahydro-cyclohepta[b]pyrrole-3-carboxamide (Compound 191).

(ttttttt) N-[4-(3 -Ethylaminopropoxy)phenyl]-4-oxo- 1,4,5,6,7,8-hexahydro-cyclohepta[b]pyrrole-3-carboxamide (Compound 192).

(uuuuuuu) N-{4-[3-(1-Phenyl-1-methylethyl)aminopropoxy]phenyl}-4-oxo-1,4,5,6,7,8-hexahydro-cyclohepta[b]pyrrole-3-carboxamide (Compound 193).

(vvvvvvv) N-[4-(Pyrid-3-ylmethoxy)pyrid-3-yl]-4-oxo-1,4,5,6,7,8-hexahydro-cyclohepta[b]pyrrole-3-carboxamide (Compound 194); mp 241–243° C.

(wwwwwww) N-[4-(Pyrid-4-ylmethoxy)pyrid-3-yl]-4-oxo-1,4,5,6,7,8-hexahydro-cyclohepta[b]pyrrole-3-carboxamide (Compound 195).

(wwwwwww-a) N-[4-(Pyrid-4-ylmethoxy)pyrid-3-yl]-4-oxo-1,4,5,6,7,8-hexahydro-cyclohepta[b]pyrrole-3-carboxamide hydrochloride (Compound 196); mp 235–240° C. (d).

(xxxxxxx) N-[4-(2-Dimethylaminoethoxy)pyrid-3-yl]-4-oxo-1,4,5,6,7,8-hexahydro-cyclohepta[b]pyrrole-3-carboxamide (Compound 197).

(yyyyyyy) N-[4-(2-Diethylaminoethoxy)pyrid-3-yl]-4-oxo-1,4,5,6,7,8-hexahydro-cyclohepta[b]pyrrole-3-carboxamide (Compound 198).

(zzzzzzz) N-[4-(2-Pyrrolidin-1-ylethoxy)pyrid-3-yl]-4-oxo-1,4,5,6,7,8-hexahydro-cyclohepta[b]pyrrole-3-carboxamide (Compound 199).

(zzzzzzz-a) N-[4-(2-Pyrrolidin-1-ylethoxy)pyrid-3-yl]-4-oxo-1,4,5,6,7,8-hexahydro-cyclohepta[b]pyrrole-3-carboxamide hydrochloride (Compound 200); mp 160–162° C.

(aaaaaaaa) N-[4-(2-Piperidin-1-ylethoxy)pyrid-3-yl]-4-oxo-1,4,5,6,7,8-hexahydro-cyclohepta[b]pyrrole-3-carboxamide (Compound 201).

(bbbbbbbb) N-{4-[2-(1-Methyl-pyrrolidin-2-yl)ethoxy]pyrid-3-yl}-4-oxo-1,4,5,6,7,8-hexahydro-cyclohepta[b]pyrrole-3-carboxamide (Compound 202).

(cccccccc) N-{4-[(1-Ethyl-pyrrolidin-3-yl)methoxy]pyrid-3-yl}-4-oxo-1,4,5,6,7,8-hexahydro-cyclohepta[b]pyrrole-3-carboxamide (Compound 203); oil.

(dddddddd) N-[4-(2-Morpholin-1-ylethoxy)pyrid-3-yl]-4-oxo-1,4,5,6,7,8-hexahydro-cyclohepta[b]pyrrole-3-carboxamide (Compound 204).

(eeeeeeee) N-[4-(2-Diethylaminoethoxy)pyrid-3-yl]-4-oxo-1,4,5,6,7,8-hexahydro-cyclohepta[b]pyrrole-3-carboxamide (Compound 205).

(ffffffff) N-[4-(2-n-Propylaminoethoxy)pyrid-3-yl]-4-oxo-1,4,5,6,7,8-hexahydro-cyclohepta[b]pyrrole-3-carboxamide (Compound 206).

(ffffffff-a) N-[4-(2-n-Propylaminoethoxy)pyrid-3-yl]-4-oxo-1,4,5,6,7,8-hexahydro-cyclohepta[b]pyrrole-3-carboxamide hydrochloride (Compound 207); mp 210° C.

(gggggggg) N-[4-(2-Isopropylaminoethoxy)phenyl]-4-oxo-1,4,5,6,7,8-hexahydro-cyclohepta[b]pyrrole-3-carboxamide (Compound 208).

(hhhhhhhh) N-[4-(3-Isopropylaminopropoxy)phenyl]-4-oxo-1,4,5,6,7,8-hexahydro-cyclohepta[b]pyrrole-3-carboxamide (Compound 209).

(iiiiiiii) N-[4-(3-Cyclopropylaminopropoxy)phenyl]-4-oxo-1,4,5,6,7,8-hexahydro-cyclohepta[b]pyrrole-3-carboxamide (Compound 210).

(jjjjjjjj) N-[4-(3-Cyclobutylaminopropoxy)phenyl]-4-oxo-1,4,5,6,7,8-hexahydro-cyclohepta[b]pyrrole-3-carboxamide (Compound 211).

(kkkkkkkk) N-[4-(3-Cyclopropylmethylaminopropoxy)phenyl]-4-oxo-1,4,5,6,7,8-hexahydro-cyclohepta[b]pyrrole-3-carboxamide (Compound 212).

(llllllll) N-[4-(3-Isobutylaminopropoxy)phenyl]-4-oxo-1,4,5,6,7,8-hexahydro-cyclohepta[b]pyrrole-3-carboxamide (Compound 213).

(mmmmmmmm) N-{4-[3-(2,2-Dimethylpropyl)aminopropoxy]phenyl}-4-oxo-1,4,5,6,7,8-hexahydro-cyclohepta[b]pyrrole-3-carboxamide (Compound 214).

(nnnnnnnn) N-{4-[3-(3-Ethylpropyl)aminopropoxy]phenyl}-4-oxo-1,4,5,6,7,8-hexahydro-cyclohepta[b]pyrrole-3-carboxamide (Compound 215).

(oooooooo) N-{4-[3-(2-Methylbutyl)aminopropoxy]phenyl}-4-oxo-1,4,5,6,7,8-hexahydro-cyclohepta[b]pyrrole-3-carboxamide (Compound 216).

(pppppppp) N-{4-[3-(2-Methylpropyl)aminopropoxy]phenyl}-4-oxo-1,4,5,6,7,8-hexahydro-cyclohepta[b]pyrrole-3-carboxamide (Compound 217).

(qqqqqqqq) N-[4-(3-i-Pentylaminopropoxy)phenyl]-4-oxo-1,4,5,6,7,8-hexahydro-cyclohepta[b]pyrrole-3-carboxamide (Compound 218).

(rrrrrrrr) N-[4-(3-Cyclohexylaminopropoxy)phenyl]-4-oxo-1,4,5,6,7,8-hexahydro-cyclohepta[b]pyrrole-3-carboxamide (Compound 219).

(ssssssss) N-{4-[3-(N-Cyclopropylmethyl,N-n-propyl)aminopropoxy]phenyl}-4-oxo-1,4,5,6,7,8-hexahydro-cyclohepta[b]pyrrole-3-carboxamide (Compound 220).

(tttttttt) N-[4-(3-Indan-2-ylaminopropoxy)phenyl]-4-oxo-1,4,5,6,7,8-hexahydro-cyclohepta[b]pyrrole-3-carboxamide (Compound 221).

(uuuuuuuu) N-[3-Fluoro-4-(2-ethoxy-2-oxoethoxy)phenyl]-4-oxo-4,5,6,7-tetrahydro-1H-indole-3-carboxamide (Compound 222); mp 192–196° C.

(vvvvvvvv) N-[3-Fluoro-4-(2-hydroxy-2-oxoethoxy)phenyl]-4-oxo-4,5,6,7-tetrahydro-1H-indole-3-carboxamide (Compound 223); mp 246–248° C.

(wwwwwwww) N-[3-Fluoro-4-(2-ethylamino-2-oxoethoxy)phenyl]-4-oxo-4,5,6,7-tetrahydro-1H-indole-3-carboxamide (Compound 224).

(xxxxxxxx) N-[3-Fluoro-4-(2-diethylamino-2-oxoethoxy)phenyl]-4-oxo-4,5,6,7-tetrahydro-1H-indole-3-carboxamide (Compound 225); mp 193–196° C.

(yyyyyyyy) N-{3-Fluoro-4-[2-(4-methylpiperizin-1-yl)-2-oxoethoxy]phenyl}-4-oxo-4,5,6,7-tetrahydro-1H-indole-3-carboxamide (Compound 226).

(zzzzzzzz) N-ethyl-N-[2-(ethylamino)ethyl]-2-{4-[(4-oxo-(4,5,6,7-tetrahydroindol-3-yl))carbonylamino]phenoxy}acetamide (Compound 227).

(aaaaaaaaa) N-[2-(dipropylamino)ethyl]-2-{4-[(4-oxo-(4,5,6,7-tetrahydroindol-3-yl))carbonylamino]phenoxy}acetamide (Compound 228); mp 148–150° C.

(bbbbbbbbb) N-[2-(diethylamino)ethyl]-N-methyl-2-{4-[(4-oxo-(4,5,6,7-tetrahydroindol-3-yl))carbonylamino]phenoxy}acetamide (Compound 229); mp 220–228° C.

(cccccccc) N-[2-(diethylamino)ethyl]-N-ethyl-2-{4-[(4-oxo-(4,5,6,7-tetrahydroindol-3-yl))carbonylamino]phenoxy}acetamide (Compound 230); mp 165–167° C.

(dddddddd) N-[4-(2-morpholin-4-yl-2-oxoethoxy)phenyl](4-oxo-(4,5,6,7-tetrahydroindol-3-yl))carboxamide (Compound 231).

(eeeeeeee) N-[3-fluoro-4-(2-morpholin-4-yl-2-oxoethoxy)phenyl](4-oxo-(4,5,6,7-tetrahydroindol-3-yl))carboxamide (Compound 232); mp 110° C.

(ffffffff) (4-oxo-(4,5,6,7-trihydroindol-3-yl))-N-[4-(2-oxo-2-piperazinylethoxy)phenyl]carboxamide (Compound 233).

(gggggggg) N-[3-(diethylamino)propyl]-2-{4-[(4-oxo-(4,5,6,7-tetrahydroindol-3-yl))carbonylamino]phenoxy}acetamide (Compound 234).

(hhhhhhhh) N-[3-(diethylamino)propyl]-2-{2-fluoro-4-[(4-oxo-(4,5,6,7-tetrahydroindol-3-yl))carbonylamino]phenoxy}acetamide (Compound 235).

(iiiiiiii) N-[4-(diethylamino)-1-methylbutyl]-2-{4-[(4-oxo-(4,5,6,7-tetrahydroindol-3-yl))carbonylamino]phenoxy}acetamide (Compound 236).

(jjjjjjjj) N-[4-(diethylamino)-1-methylbutyl]-2-{2-fluoro-4-[(4-oxo-(4,5,6,7-tetrahydroindol-3-yl))carbonylamino]phenoxy}acetamide (Compound 237).

EXAMPLE 4

Water solubility for various compounds within the invention was determined and compared with that for compounds outside the scope of the invention. The compounds evaluated are encompassed within formula II:

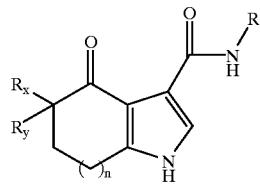

II

| Water Solubility (μg/ml) | $R_x$ | $R_y$ | n | R |
|---|---|---|---|---|
| 23 | H | H | 1 | 4-(2-hydroxyethoxy)phenyl |
| 203 | H | H | 1 | 3-(methylaminomethyl)phenyl |
| 143 | H | H | 2 | 4-(methylaminomethyl)phenyl |
| 15 | H | H | 1 | 4-(isopropylaminomethyl)phenyl |
| 1.0 | H | H | 1 | 4-fluorophenyl |

-continued

| Water Solubility (µg/ml) | $R_x$ | $R_y$ | n | R |
|---|---|---|---|---|
| 0.58 | H | H | 1 | 4-methylbenzyl |
| 0.34 | H | H | 1 | 4-ethoxybenzyl |
| 0.26 | $CH_3$ | $CH_3$ | 1 | 2-fluoro-4-methoxybenzyl |

The invention and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the spirit or scope of the present invention as set forth in the claims. To particularly point out and distinctly claim the subject matter regarded as invention, the following claims conclude this specification.

What is claimed is:

1. A compound of the formula

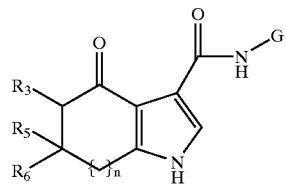

where G represents

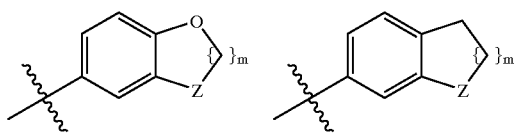

where where Z is nitrogen, or methylene; and m is 1 or 2; and $R_3$, $R_5$, and $R_6$ are the same or different and are selected from hydrogen, alkyl, $-COR_{11}$ or $CO_2R_{11}$ where $R_{11}$ is alkyl or cycloalkyl having 3–7 carbon atoms; or $-CONR_{12}R_{13}$ where $R_{12}$ and $R_{13}$ are selected independently from hydrogen, alkyl, cycloalkyl having 3–7 carbon atoms, phenyl, 2-, 3-, or 4-pyridyl or $NR_{12}R_{13}$ form a heterocyclic group which is morpholinyl, piperidinyl, pyrrolidinyl, or N-alkyl piperazinyl; or $R_5-R_6$ may be taken together to form a cyclic moiety having 3–7 carbon atoms; and where each alkyl group forming an $R_3$ $R_5$, or $R_6$ substituent or portion thereof may be substituted independently with hydroxy or mono- or dialkylamino where each alkyl is independently alkyl or cycloalkyl having 3–7 carbon atoms.

2. A compound according to claim 1, which is N-(2,3-Dihydro-1H-indol-6-yl)-4-oxo- 4,5,6,7-tetrahydro-1H-indole-3-carboxamide.

* * * * *